United States Patent [19]

Poore

[11] Patent Number: 5,697,959
[45] Date of Patent: Dec. 16, 1997

[54] METHOD AND SYSTEM FOR ANALYZING AND DISPLAYING COMPLEX PACING EVENT RECORDS

[75] Inventor: John W. Poore, South Pasadena, Calif.

[73] Assignee: Pacesetter, Inc., Sylmar, Calif.

[21] Appl. No.: 584,574

[22] Filed: Jan. 11, 1996

[51] Int. Cl.$^6$ .............................. A61N 1/362; A61N 1/37
[52] U.S. Cl. ..................................... 607/32; 607/30
[58] Field of Search .................................... 128/710, 712; 607/27, 30, 32

[56] References Cited

U.S. PATENT DOCUMENTS

| | | | |
|---|---|---|---|
| 4,559,947 | 12/1985 | Renger et al. | 607/32 |
| 4,596,255 | 6/1986 | Snell et al. | 128/697 |
| 4,791,936 | 12/1988 | Snell et al. | 128/697 |
| 4,809,697 | 3/1989 | Causey et al. | 128/419 |
| 4,944,299 | 7/1990 | Silvian | 128/419 |
| 5,292,341 | 3/1994 | Snell | 607/30 |
| 5,309,919 | 5/1994 | Snell et al. | 128/697 |
| 5,372,607 | 12/1994 | Stone et al. | 607/30 |
| 5,425,373 | 6/1995 | Causey | 128/697 |
| 5,431,691 | 7/1995 | Snell et al. | 607/27 |
| 5,447,164 | 9/1995 | Shaya | 128/710 |
| 5,487,754 | 1/1996 | Snell et al. | 607/27 |
| 5,487,755 | 1/1996 | Snell et al. | 607/27 |
| 5,549,654 | 8/1996 | Powell | 607/32 |

*Primary Examiner*—William E. Kamm
*Assistant Examiner*—Carl H. Layno

[57] ABSTRACT

A method and system for analyzing and displaying pacing event data of an implantable pacemaker using a programmer device comprises downloading the pacing event data from the implantable pacemaker to the programmer device and processing the pacing event data to produce an Event Record. The Event Record includes actual pacing event data obtained and stored by the implantable pacemaker over a prescribed period of time as well as various statistical information derived therefrom. Selected parametric data of the Event Record are then displayed to the physician or other user on a display screen of the programmer device in a simple and comprehensible graphical format.

23 Claims, 10 Drawing Sheets

METHOD AND SYSTEM FOR ANALYZING AND DISPLAYING COMPLEX PACING EVENT RECORDS

BACKGROUND OF THE INVENTION

The present invention relates to data analysis systems and methods for use with implantable medical devices, and more particularly to a data analysis system for use with an implantable pacemaker that analyzes and displays a summary of pacing event information collected over a prescribed period of time. The pacing event information includes data relating to prescribed parameters recorded by the implantable pacemaker as such pacing events occur, either on an every event basis or on a sampled basis over time. The pacing event information is retrieved from the pacemaker, processed, and displayed in a manner that is useful as a diagnostic tool for analyzing the performance of the pacemaker and for aiding physicians in optimally programming the pacemaker for a particular patient.

One of the most common types of implantable medical devices in use today is the implantable pacemaker. Modern pacemakers are small, battery-powered electronic devices that monitor the activity of the heart to determine when the heart is naturally beating, and provide stimulation pulses to the heart when the heart is not naturally beating, thereby maintaining a prescribed heart rhythm or rate. Advantageously, a pacemaker may be implanted in a patient, and coupled to the patient's heart via appropriate pacemaker leads that are also implanted. By implanting the pacemaker and leads, the pacemaker becomes an integral part of the patient, and the patient is able to maintain a substantially normal life style without the bother and worry that typically accompany the use of external or non-implanted, life-sustaining medical devices.

Nearly all implantable pacemakers in use today, as well as similar implantable medical devices, can be configured by the attending physician in the physician's office. The process of configuring a pacemaker is commonly referred to as "programming" the pacemaker. The programming process currently uses noninvasive telemetry to customize the operation of the pacemaker to fit the individual needs of the patient. Customization is achieved by adjusting a set of programmable parameters to values that cause the pacemaker to work in an optimum way for the particular patient within whom the pacemaker has been implanted.

As the complexity of new implantable devices has evolved over the past several years, it has become increasingly difficult for the attending physician, or other medical personnel, to determine how the pacemaker should be programmed in order to provide the most effective therapy for a given patient. This difficulty is particularly manifest with recent-generation pacemakers that tend to be more automatic and autonomous than earlier-generation pacemakers, which recent-generation pacemakers may be controlled by input signals received from a multiplicity of internal sensors. For example, recent "rate-responsive" pacemakers provide stimulation pulses to a patient's heart, as needed, based on the input signals received from one or more physiological or other sensors that attempt to predict just how fast the patient's heart should beat in order to meet the patient's physiological needs.

A significant factor that makes the optimum programming of recent-generation pacemakers more difficult is the variation in each of the sensor inputs from patient to patient. Such variation is caused by numerous factors, including the patient's physical structure, the implant site, the particular disease or malady the patient has and its progression within the patient's heart or other body tissue, the drugs being taken by the patient to treat his or her condition, etc. Thus, to appropriately program the pacemaker for a given patient, the physician must anticipate how the pacemaker will operate given all of these variables, and given all the environments and activities that the patient is expected to encounter. Programming a modern pacemaker may thus comprise an extremely formidable task, for which task there is a critical need for programming aids to assist the physician in anticipating the pacemaker response for each particular patient.

It is known in the art to use programming aids and devices with implantable pacemakers to facilitate the physician's understanding of the pacemaker's programmed operation as its interacts with the patient's natural cardiac activity. For many years, the primary programming aid and source of diagnostic data for use in analyzing the operation of an implanted pacemaker has been the surface electrocardiogram (ECG), in which both pacemaker and heart activity are blended. From the ECG, the activity of the heart, i.e. the contraction of the atria, the contraction of the ventricles, and the timing therebetween, could be displayed. From the pacemaker, the activity of the pacemaker including when a heart contraction was sensed and when a stimulation pulse was generated could likewise be monitored through the use of marker signals telemetered from the pacemaker to a remote or non-implanted receiver. The marker signals were appropriately processed and displayed as marks on the ECG waveform.

In recent years, specific programming devices have been developed that not only allow the pacemaker parameters to be noninvasively set to desired values, but that also allow the operation of the pacemaker and the heart to be monitored without having to obtain a surface ECG. Such is accomplished by transmitting an intracardiac ECG signal, either alone or in combination with marker signals. See e.g., U.S. Pat. Nos. 4,559,947; 4,596,255; 4,791,936; and 4,809,697.

While such prior art programming devices have done much to facilitate communications with and analysis of implantable programmable pacemakers, they all suffer from one major drawback, namely, they are limited to real-time data analysis. This is true even though some provide the capability of capturing a short segment, e.g., 30 seconds, of the intracardiac ECG signal, which intracardiac ECG signal, once captured, can advantageously be expanded, compressed, or otherwise processed in a desired manner in order to better examine it. Unfortunately, in order to properly assess some types of problems that may develop for a given patient having an implanted pacemaker, it is frequently necessary to examine the intracardiac ECG signal, or at least the main components thereof, over a much longer period of time, e.g., minutes, hours, days, weeks, or months.

More recently, there have been developed pacemakers having the capability to count or record the number of times that a given pacing event occurs or a state change of the pacemaker occurs. Likewise, there are pacing devices that continuously and sequentially record pacing event information. The pacing event information is typically retained in a pacemaker memory or other buffer associated with the pacemaker and is periodically downloaded to a specialized programmer device. These and other pacemakers are now designed with increasing amounts of memory used for storing both raw pacing event data as well as pre-processed diagnostic information, such as the above-mentioned event counts. Currently, pacemakers are designed to store about 4000 bytes of data or less. The memory and data handling capability of pacemakers should rapidly increase to 20,000 bytes or more due to the advancement in memory chip technology.

While many improvements have been made to recent pacemakers, including on-site processing and storage of data, proportionally fewer advancements have been incorporated into the programmer device as it relates to the analysis and display of the data available from the pacemakers. Recent advancements in the field of analysis and display of pacemaker related data has primarily focused on processing and analysis of the intracardiac ECG signals and/or the mere counting and display of pacing events and the frequency thereof. See, for example, U.S. Pat. Nos. 5,425,373; 5,309,919; and 5,431,691.

Disadvantageously, however, such methods and systems are limited in that they merely display the total occurrences and the frequency of occurrence or rate of the cardiac events that are recorded by the pacemaker. These systems do not provide on-demand detailed analysis and displays relating to numerous other parameters and statistical information (i.e. minimum value, maximum value, median value, average value, standard deviation, etc.) associated therewith. Such limitations prevent numerous evaluations and assessments from being performed on-demand by the physician or other medical personnel. Conversely, the vast amount of data available from an implanted pacemaker can be overwhelming and somewhat confusing to many physicians. Moreover, many physicians do not take the time to become thoroughly familiar with the operation of computer-based data analysis systems. Thus, if such a system is not simple to operate and does not display the data in understandable and useful formats, many physicians will use alternative diagnostic tools.

What is needed therefore, is a system or a method or both for displaying the vast amount of parameter data retrieved from a pacemaker or other implantable device in a simple, comprehensible and versatile format. The display content and format must facilitate the physician's ability to understand the presented data as it relates to the interaction of the implanted device with the patient and to evaluate active clinical problems. In addition, the display should provide the physician or other medical personnel with sufficient data to allow the performance of the implanted device to be assessed over an extended period of time.

Moreover, in some instances, it may be necessary, or at least desirable, if a proper analysis of a particular problem is to be made, to carefully examine selected parameters at a particular moment in time, which particular moment in time may have occurred several hours or days ago. Such analysis could reveal, for example, whether a premature ventricular event or other anomaly occurred, or if a particular cardiac cycle was made up of paced events or sensed events, or both. Hence, there is also a continuing need for improved diagnostic tools that allows the past interaction between a pacemaker and a patient's heart to be thoroughly examined and studied.

SUMMARY OF THE INVENTION

The present invention addresses the above and other needs by providing a method and system for displaying an Event Record of an implantable pacemaker using a programmer device. The method of the invention involves downloading the pacing event data from the implantable pacemaker to the programmer device and subsequently processing the pacing event data to produce an Event Record. This Event Record is stored in a designated portion of memory in the programmer device. Various parameters of the Event Record are then displayed to the physician or other user on a display screen of the programmer device in a simple and comprehensible graphical format.

The Event Record preferably includes a multiplicity of parameters and corresponding parametric data derived from the operation of the implantable pacemaker over a prescribed period of time. The parametric data includes actual pacing event data obtained and stored by the implantable pacemaker, as well as various statistical information derived therefrom. The statistical information may include, for example, minimum values, maximum values, averages, median values, standard deviations, etc.

Specifically, the information displayed on the display screen selectively includes a graph of the parametric data over a given time period which is generated and displayed based on user selections of the parameter or parameters to be displayed, together with an appropriate time scale. The user selections are made from various selection tables concurrently displayed with the parametric data on the display screen. The physician or other user selects any one or more of the many parameters contained in the Event Record from a first selection table in the selection table in order to display the parametric data associated with such parameter or parameters in a graphical format. In addition, the physician selects an appropriate time scale from a second selection table that is to be the abscissa of the graph to be displayed.

Advantageously, the physician or other user can readily change the displays presented by merely selecting a different time scale, a different parameter, or both. Moreover, the process of changing the time scale and/or selected parameter is made simple because both the parameter selection table and the time scale table are concurrently displayed with the graphical representation of the currently selected parameter.

The present system and method of analyzing and displaying complex pacing Event Records is adapted to be used in conjunction with an implanted device, such as a recent generation dual-chamber pacemaker, that continuously records pacing event data. The pacing event data recorded by the implanted device comprise a plurality of records each corresponding to a specific pacing event associated with the operation of the implanted pacemaker. Such pacing events are typically recorded in sequence, as they occur, in an internal memory or other buffer area of the implantable pacemaker. The recording of the pacing events may selectively occur at every event, for highest resolution and highest memory utilization, or at sampling rates of one event per fixed sample interval.

In accordance with one aspect of the invention, an external programming device is selectively coupled to an implantable pacemaker through a telemetry link. The programming device includes processing means for retrieving the recorded pacing event data stored in the pacemaker. Since the programming device retrieves the data from the implantable pacemaker at a known reference time and the pacing event data was collected on a predetermined sample interval, the programming device is able to assign a time of occurrence to all the pacing event data sequentially collected by the pacemaker. This time of occurrence is stored as part of the Event Record together with corresponding parametric data during the initial processing of the data on the programmer device. Thus, the parametric data of the Event Record can be displayed as a function of time of occurrence. The physician may then use this information concerning past behavior to reliably predict future behavior. Such reliable prediction thus guides the physician as he or she programs the pacemaker for optimum performance relative to the individual patient.

One embodiment of the invention may simply be characterized as an external programming device for analyzing and displaying complex pacing Event Records. Such external programming device includes: (1) a telemetry head and communication circuitry that selectively retrieves the pacing event data stored in the memory of the implantable pacemaker, (2) a data processor controlled by an operating program that processes the pacing event data to produce Event Records, the Event Records including a multiplicity of parameters and corresponding parametric data derived from the operation of the implantable pacemaker over a prescribed period of time, (3) a memory for storing the operating program and the Event Records, (4) a means for selecting one or more of the multiplicity of parameters contained in the Event Records together with a time scale in which the corresponding parametric data is to be displayed, and (5) a display screen coupled to the data processor on which the selected parametric data of the Event Records are displayed in a graphical format.

An important feature of the disclosed programming device is that it places a time stamp on the sequence of pacing events stored within the implantable pacemaker when such events are retrieved and processed, thereby allowing such events to be analyzed and displayed as a function of the time when such pacing events occurred.

Another feature found in the disclosed embodiment of the programming device is the capability to selectively scroll the displayed graph along the selected time scale or abscissa. In one embodiment, multiple "left" or "right" scroll buttons can be activated which causes the graphical display of parametric data to scroll "left" (corresponding to a "backwards-in-time" scroll) or "right" (corresponding to a "forward-in-time" scroll). In addition, the scroll buttons when activated can cause scrolling of the display at one of a plurality of scrolling rates (i.e., fast or slow).

Still another feature of the embodiments of the programming device contemplate the use of identification markers to identify a selected point of the displayed graph so that the corresponding parametric data of the selected point can be displayed in tabular form. Although many different types of identification markers are contemplated, the preferred identification marker is a vertical line marker that remains at a fixed location on the display screen as the graph is selectively scrolled along the abscissa.

Another embodiment of the invention comprises a pacing system that includes both an implantable pacemaker and an external programming device configured to monitor and report the occurrence of cardiac pacing events over time; and, upon command, provide such information to an attending physician in a simple and comprehensible format. Advantageously, such system allows the past interaction between the pacemaker and a patient's heart during a prescribed time period to be carefully examined and studied, where the past interaction is defined by specified pacing events and various statistical information associated therewith.

BRIEF DESCRIPTION OF THE DRAWINGS

The above and other objects, features and advantages of the present invention will be more apparent from a thorough consideration of the detailed description thereof presented in conjunction with the following drawings in which.

Corresponding reference characters indicate corresponding components throughout the several views of the drawings.

DETAILED DESCRIPTION OF THE INVENTION

Figure 1:
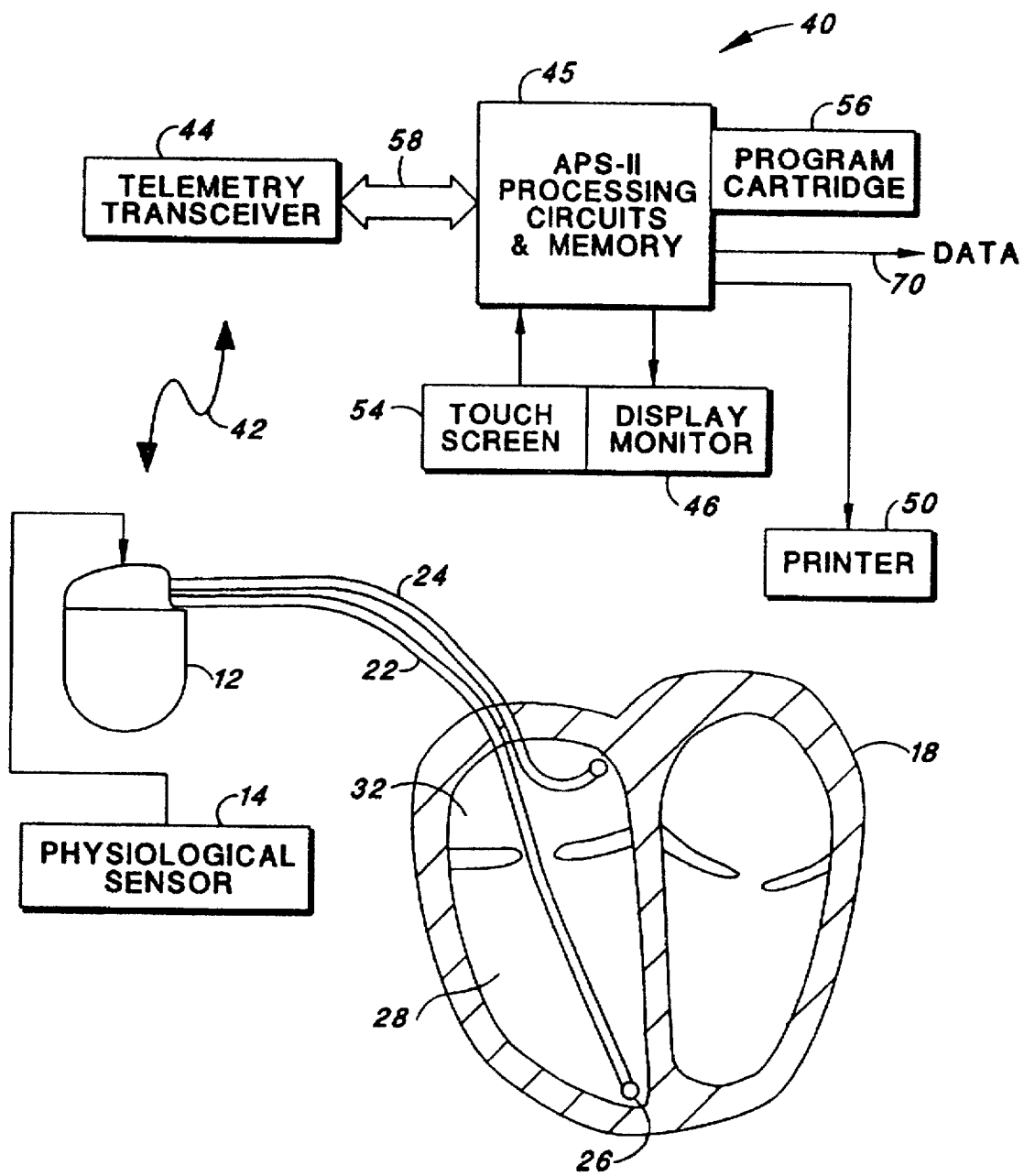
FIG. 1 is a block diagram showing the main components of a cardiac pacing and programming system.

The following description is of the best mode presently contemplated for carrying out the invention. This description is not to be taken in a limiting sense, but is made merely for the purpose of describing the general principles of the invention. The scope of the invention should be determined with reference to the claims.

Before describing the various embodiments of the present invention in more detail, it will be helpful to understand recent developments in pacing systems as well as the basic structure and operability of an implantable pacemaker and associated programmer device. A pacemaker is an implantable medical device that delivers electrical stimulation pulses to a patient's heart, as required, in order to keep the heart beating at a desired rate. Early pacemakers provided stimulation pulses at a fixed rate or frequency, such as 70 pulses per minute (ppm), thereby maintaining the heart beat at that fixed rate. Subsequently, pacemakers were designed to not only stimulate the heart, but also to monitor the heart. If a natural heart beat was detected within a prescribed time period, then no stimulation pulse is delivered, thereby allowing the heart to beat on its own without consuming the limited power of the pacemaker. Such pacemakers are referred to as "demand pacemakers" because stimulation pulses are provided only as demanded by the heart.

Early demand pacemakers had a fixed base rate associated therewith. In later versions, the base rate was programmably selectable, and thereafter became commonly known as the programmed rate. If the heart was able to beat on its own at a rate exceeding the base or programmed rate, then no stimulation pulses were provided. However, if the heart was not able to beat on its own at a rate exceeding the base rate, then stimulation pulses were provided to ensure that the heart would always beat at least at the base or programmed rate.

In recent years, rate-responsive pacemakers have been developed that automatically change the rate at which the pacemaker provides stimulation pulses as a function of a sensed physiological parameter. The physiological parameter provides some indication of whether the heart should beat faster or slower, depending upon the physiological needs of the pacemaker user. Thus, for example, if a patient is at rest, there is generally no need for a faster than normal heart rate, so the rate-responsive pacemaker maintains the base or programmed rate at a normal value, such as 60 ppm. However, if the patent is exercising, or otherwise physiologically active, there is a need for the heart to beat much faster, such as 100 beats per minute. For some patients, the heart is not able to beat faster on its own, so the pacemaker must assist. In order to do this effectively, the physiological need for the heart to beat faster must first be sensed, and the base or programmed rate of the rate-responsive pacer must be adjusted to the desired level. Hence, rate-responsive pacemakers are known in the art that increase and decrease the base or programmed rate as a function of sensed physiological need.

Referring now to the drawings, and particularly FIG. 1, an illustrated pacing system has a pacemaker side and a programmer side. As seen in FIG. 1, an implantable pacemaker 12 preferably has a physiological sensor 14 coupled to the pacemaker 12. It is to be understood, however, that the present invention may be used with pacemakers that do not have a sensor 14 coupled thereto, or to pacemakers wherein such a sensor 14 has been programmed to an OFF or PASSIVE mode, such terms being more fully defined below. The pacemaker 12 is also coupled to the heart 18 by way of pacing leads 22 and 24. The pacing lead 22 has an electrode 26 positioned in the right ventricle 28 of the heart 18. The lead 22 is thus typically referred to as the ventricular lead, and the signals generated by the implantable pacemaker for delivery to the heart through electrode 26 over lead 22, or the signals sensed through electrode 26 and the lead 22, are processed by circuits in what is known as the ventricular channel of the pacemaker 12. Similarly, the pacing lead 24 has an electrode 30 positioned in the right atrium 32 of the heart 18. The lead 24 is thus typically referred to as the atrial lead, and the signals generated by the pacemaker 12 for delivery to the heart through the electrode 30 over lead 24, or the signals sensed through electrode 30 and the lead 24, are processed by circuits in what is known as the atrial channel of the pacemaker 12.

Note that what is shown in FIG. 1 is a dual-chamber pacemaker, in that sensing and/or pacing may occur in both chambers of the heart 18, i.e., in the atrium 32 and/or the ventricle 28. It is to be understood that the present invention may be used with either dual-chamber pacing, as shown in FIG. 1, or with single chamber pacing, where sensing and pacing occur in only one chamber of the heart. It should also be understood that most pacemakers that provide a dual-chamber configuration, such as is illustrated in FIG. 1, may also be programmed to operate in a single chamber mode.

As suggested in FIG. 1, the pacemaker 12 is in telecommunication contact with an external programmer 40 via a telemetry link 42. The programmer 40 includes a telemetry transceiver 44, processing circuits 45, and display monitor 46 external to the patient's skin. The programmer 40 may also have a printer 50, touch screen 54, and a removable program cartridge 56, described in more detail below.

The pacemaker 12 includes a telemetry subsystem (not shown) for transmitting pacing event data records to the external telemetry transceiver 44 of the external programmer 40, and for receiving command signals and other instructions from the external programmer 40. Command signals received from the external programmer 40 are decoded in an appropriate encoder/decoder (not shown) and processed accordingly. Likewise, pacing event data records to be sent to the external programmer 40 are preferably encoded prior to transmission. The manner in which one would establish and operate a telemetry link 42 between an external programmer 40 and a pacemaker 12 is generally known in the art.

Figure 2:
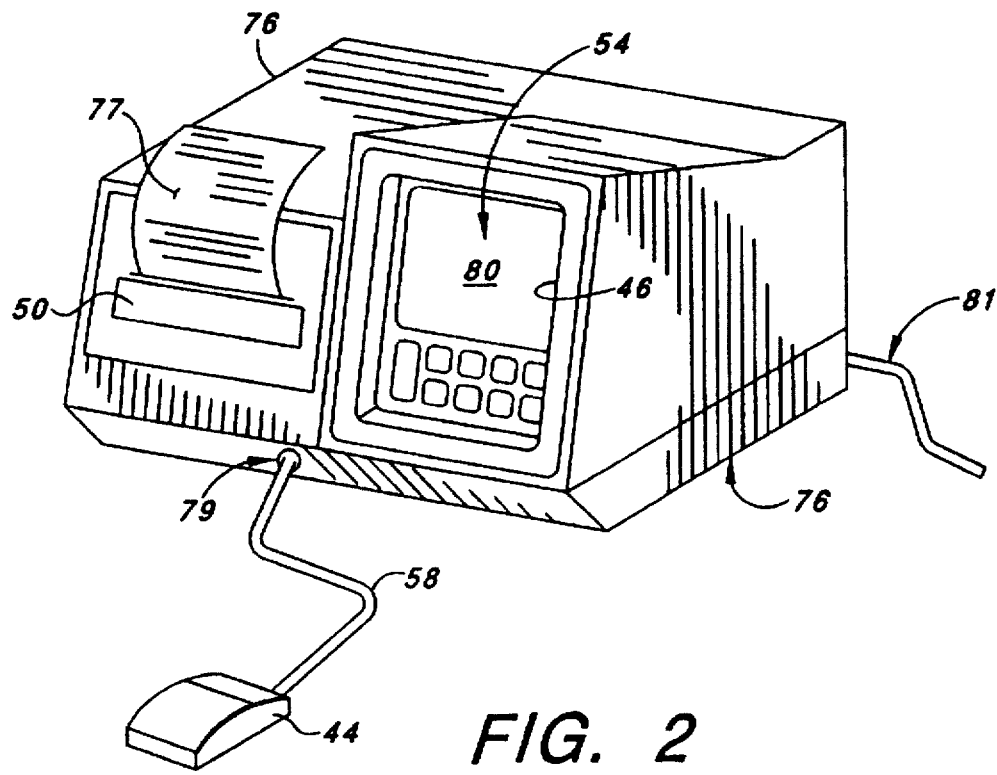
FIG. 2 is a perspective view of an external programmer, referred to herein as the "APS-II", that may be used with an implantable pacemaker.

The preferred external programmer 40 used with the present invention is hereafter referred to as an analyzer-programmer system (APS). A preferred model of the APS is the APS-II, manufactured and sold by Pacesetter, Inc., of Sylmar, Calif. FIG. 2 shows a perspective view of the external programmer. A more complete description of a similar external programmer 40 may be found in U.S. Pat. No. 4,809,697, which patent is also incorporated herein by reference. The APS-II provides a sophisticated, microprocessor-based programming system that can be used to noninvasively interrogate and program the programmable, implantable pacemakers manufactured by Pacesetter, Inc. However, while the APS-II represents the preferred embodiment and best mode of the programmer 40, it is to be understood that other models and types of external programmers can and will exist with which the present invention may be used.

As described above, the pacemaker 12 is a self-contained unit capable of both sensing natural cardiac activity and providing stimulation pulses to invoke paced cardiac activity. The operating characteristics of the pacemaker 12 can be noninvasively programmed by way of command signals received over telemetry link 42, which command signals are received from a telemetry transceiver 44 connected to the APS-II processing circuits 45 by way of a connection cable 58. The command signals are generated within the APS-II processing circuits 45 as a function of operating commands received by way of a touch sensitive screen 54. That is, an APS-II operator selects a desired command by touching a designated area on the touch screen 54, which designated area is defined by a particular pattern displayed on a display monitor 46. Advantageously, the touch screen 54 overlays a screen of the display monitor 46 so that all one need do to make a command selection is to touch the screen of the monitor 46 at the area indicated on the display for the desired command.

The pacemaker 12 is also capable of sending operating data, measured data, and other signals over the telemetry link 42 to the telemetry head or transceiver 44. The telemetry transceiver 44 preliminarily processes the incoming signals and forwards them to the APS-II processing and memory circuits 45. Data and other signals received at the APS-II circuits 45 may be displayed on the display monitor 46, printed on a printer 50, and/or stored within the memory elements of the APS-II circuits 45 for subsequent retrieval and display. Alternatively or conjunctively, pacing event data received at the APS-II circuits 45 may be transmitted over an appropriate data channel 70 to a desired external device, such as a modem, an X-Y plotter, a tape or disk drive, a personal computer, or other peripheral device.

Operation of the APS-II processing and memory circuits is typically controlled by way of a program cartridge 56 that is detachably connected to the processing and memory circuits 45. This removable program cartridge 56 thus advantageously allows the operating characteristics of the APS-II device to be easily upgraded to include new features and to properly interface with new pacemakers, as new features and new pacemakers are developed. Such upgrading can occur at minimal cost because all that is required is a new program cartridge 56, rather than a whole new analyzer-programming system 40, as has been required in the past. The present invention, relating to a method and system for analyzing and displaying complex Event Records over time, is facilitated through the use of a such new program in a new program cartridge 56.

FIG. 2 illustrates a housing 76 within which the APS-II system components are housed. In accordance with one embodiment, all of the circuits of the APS-II processing circuits and memory 45, including the printer 50, the display screen 46, the touch screen 54, and the program cartridge 56, are housed within the housing 76. The telemetry transceiver 44 is coupled to the housing 76 by way of cable 58. As seen in FIG. 2, the preferred display screen 46 is a CRT display monitor 80, over which touch screen 54 is laid, provides a readily visible and accessible means for viewing displays and selecting commands. Similarly, the printer 50 provides a paper copy 77 of that which is displayed on the screen of the CRT 80, or other desired information, as selected by the commands available through touching the touch screen 54. The telemetry transceiver 44 is attached to cable 58 which plugs into a connector 79 located on the bottom front side of the housing 76. A power cord 81 similarly plugs into socket at the rear of the housing and allows the APS-II to be powered from any suitable electrical outlet. The power cord 81 may be stored on the bottom of the housing 76 for ease of transportation and storage. Similarly, the telemetry head 44, when detached, can be stored in a removable front cover (not shown) when not in use.

With the above overview of a pacing system in mind, it may be helpful to review some basic definitions used in this application that relate to the operation of pacemakers. A "P-wave" is an electrical signal manifest when the atrium contracts naturally. An "R-wave" is an electrical signal manifest when the ventricle contracts naturally. An "A-pulse" is an electrical stimulation pulse that is generated by the pacemaker and delivered to the atrium in order to force an atrial contraction. A "V-pulse" is an electrical stimulation pulse that is generated by the pacemaker and delivered to the ventricle in order to force a ventricular contraction. A "cardiac cycle" is the time it takes the heart to cycle through one complete sequence of atrial and ventricular contractions. A "pacing cycle" is a cardiac cycle as measured or determined within the pacemaker. The cardiac or pacing cycle may be measured between any two recurring points or events associated with such sequence of contractions, such as P-waves, R-waves, A-pulses, V-pulses, or combinations thereof. The cardiac cycle may be represented by an A-pulse followed by a V-pulse, by an A-pulse followed by an R-wave, by a P-wave followed by a V-pulse, or by a P-wave followed by an R-wave.

Continuing with the definition of terms, a "PVE" is a premature ventricular event, i.e., an R-wave that occurs without an intervening P-wave or A-pulse. The "MTR" is the maximum tracking rate of the pacemaker, and defines a minimum time interval that must elapse after a specified cardiac event, e.g., an R-wave or a V-pulse, before another paced event (A-pulse or V-pulse) is allowed to take place. The "MSR" is the maximum sensor rate, and is used in conjunction with rate-responsive pacemakers to define the maximum base-rate that the pacemaker may assume. Both the MTR and the MSR are parameters used to limit the maximum rate at which a pacemaker is allowed to provide stimulation pulses on demand.

There are five important operational states associated with the operation of the pacemaker when configured for operation in a dual-chamber mode. Three of these operative states relate directly to cardiac or paced activity that occurs in the atrium and two relate to activity that occurs in the ventricle. The three atrial states are: (1) atrial pulse (A-pulse); (2) sensed P-wave; and (3) sensed P-wave during the Maximum Tracking Rate. The two ventricle states are: (4) ventricular stimulation pulse (V-pulse); and (5) sensed R-wave. Advantageously, the changing from one operational state to another operational state signals the occurrence of a particular event and are considered as "pacing events". Such pacing events are recorded in sequence as they occur, or at a specified sampling rate. The pacing event data are stored in the pacemaker memory in such a way that they can be retrieved in the same order in which they were stored or alternatively in the reverse order in which they were stored. It is important to note that a given pacemaker may have numerous other states associated with the operation thereof. While important to the operation of the implantable pacemaker, these additional states have little relevance to the present embodiment of a system and method for analyzing and displaying complex pacing Event Records.

The five operational states of the dual-chamber pacemaker identified above define a plurality of pacing events. There are four basic pacing event types that are recorded by the pacemaker associated with the present invention. These are: (1) a P-wave followed by a V-pulse (referred to as a "PV" event); (2) a P-wave followed by an R-wave (referred to as a "PR" event); (3) an A-pulse followed by a V-pulse (referred to as an "AV" event); and (4) an A-pulse followed by an R-wave (referred to as an "AR" event). In addition to the above four basic pacing event types, three other pacing events may be defined. These other three pacing event types are: (5) a premature ventricular event (referred to as a "PVE") and defined as an R-wave that occurs without an appropriate intervening atrial event; (6) a P-wave at the maximum tracking rate followed by a V-pulse (referred to as a "P@MTR-V" event); and (7) a P-wave at the maximum tracking rate followed by an R-wave (a "P@MTR-R" event). Typically, a "P@MTR-V" event may be considered as a "PV" event; and a "P@MTR-R" event may be considered as a "PR" event.

Because the pacing events defined above are reflected in prescribed operational state changes of the pacemaker, the occurrence of such events can be readily determined by monitoring the pacemaker for the prescribed operational state changes. In particular, the occurrence of any of the above-defined seven pacing events is stored in a pacemaker memory. As the pacing events are stored, they are stored as a fixed length pacing event data record having a plurality of fields. A first field identifies the pacing event type. A second field may, for example, identify the cardiac or pacing cycle time. Likewise, additional fields may contain specified pacing event parametric values.

Appropriate circuitry within the pacemaker, and particularly within the memory of the pacemaker, stores the pacing event data in the proper sequence and with the proper event designator and parametric value. Appropriate commands received from the external programmer allow the pacing event data to be downloaded to the external programmer. Preferably, a two-bit code held in a designated location of the pacemaker memory specifies whether the sampling rate is every event (code 00), every 1.6 seconds (Code 01), every 26 seconds (code 10) or other designated sample rate (code 11).

The sampling period preferably lasts for a complete cardiac cycle as measured by the occurrence of two ventricular states (i.e. V-pulse or R-wave). Within each sample period the occurrence of the first atrial state (A-pulse or P-wave) and the immediately successive ventricle state constitutes the sampled pacing event. The occurrence of the second ventricle state is used to determine the cardiac cycle time relating to the sampled pacing event.

As indicated above, a premature ventricular event occurs when an R-wave occurs without an appropriate intervening atrial state. In such circumstances, the sampled event is a "PVE" and the cardiac cycle time is measured using the two successive ventricular states. Parametric data relating to the "PVE" is recorded at the occurrence of the first ventricle event. At the end of each sampling period, the pacing event data, including event designation, cycle time and other parametric values, are stored in the pacemaker memory. If the sampling rate is set to "Every Event" (code 00) then the sampling period becomes the event's cycle interval, meaning a recording clock within the pacemaker has an appropriate cycle time coincident with each paced or sensed event, and pacing event data are stored at the end of each paced or sensed event.

Figure 3:
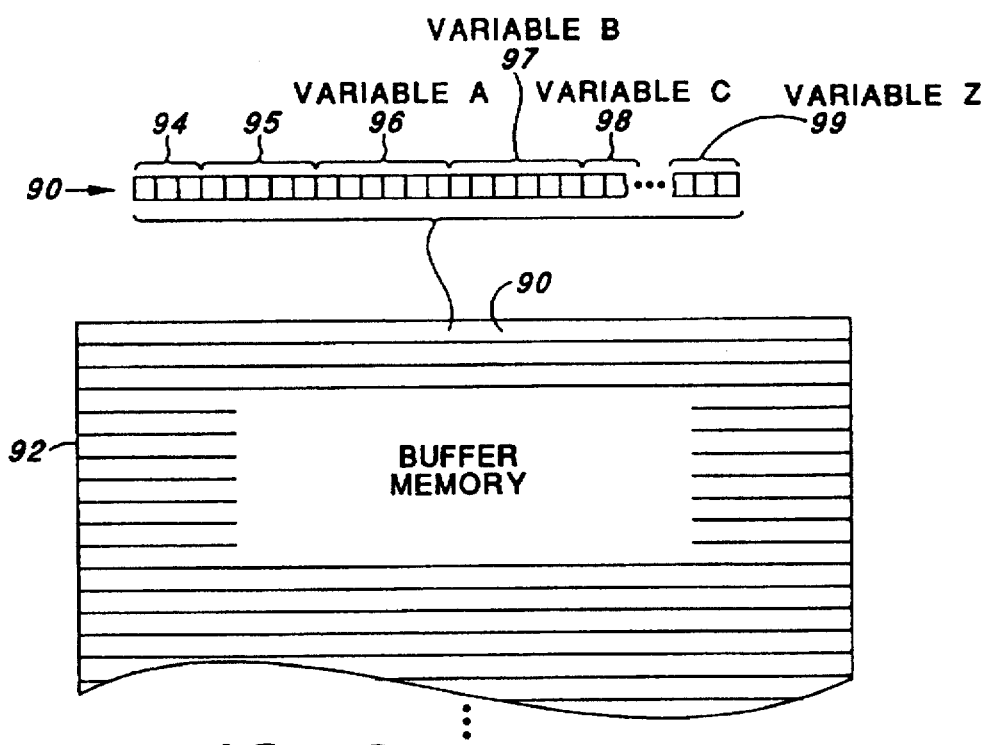
FIG. 3 is a schematic illustration of the organization of representative pacing event data records as stored in the memory of a pacemaker and telemetered or downloaded to the external programmer.

Turning now to FIG. 3, each pacing event data record 90 stored in the buffer memory 92 has a prescribed format associated therewith. For example, the data record 90 may comprise a fixed length record having a plurality of designated fields. A first field 94, bits 0–2, contains the Event Type Designator. Event Type Designators are 3-bit values in the range of 000 to 110 (representing numbers 0 through 6) which correspond to a particular Event Type. Representative Event Type Designators for the pacing events that may be monitored by the present invention are defined in Table 1.

TABLE 1

Pacing Event Data Identification

| Event No. | Bit Sequence | Event Designation | Event Description |
|---|---|---|---|
| 0 | 000 | AV | A-Pulse followed by V-Pulse |
| 1 | 001 | AR | A-Pulse followed by R-wave |
| 2 | 010 | PVE | Premature Ventricular Event |
| 3 | 011 | PV | P-Wave followed by V-Pulse |
| 4 | 100 | PR | P-Wave followed by R-wave |
| 5 | 101 | P@MTR-V | P-Wave at Maximum Tracking Rate followed by V-Pulse |
| 6 | 110 | P@MTR-R | P-Wave at Maximum Tracking Rate followed by R-Wave |

The second field 95 in each pacing event record 90 is bits 3–7. This field contains the cardiac or pacing cycle time. The preferred pacing cycle times are 5-bit values in the range of 0–31 that represent the pacing cycle time corresponding to each pacing event. The lowest Cycle Time value of 0 represents a pacing interval of approximately 323.7 msec (or 185.3 ppm). Each successive value increments the interval by approximately 25.3 msec. The highest value of 31 represents 1110.8 msec (or 54 ppm). Table 2 lists the interval time for each cycle time value.

TABLE 2

Pacing Event Data Cycle Times

| Bin No. | Bit Sequence | Range, MSec. | Range, PPM |
|---|---|---|---|
| 0 | 00000 | 323.7–342.8 | 185.3–175.0 |
| 1 | 00001 | 349.1–368.2 | 171.9–163.0 |
| 2 | 00010 | 374.5–393.6 | 160.2–152.5 |
| 3 | 00011 | 399.9–418.9 | 150.0–143.2 |
| 4 | 00100 | 425.3–444.3 | 141.1–135.0 |
| 5 | 00101 | 450.7–469.7 | 133.1–127.7 |
| 6 | 00110 | 476.1–495.1 | 126.0–121.2 |
| 7 | 00111 | 501.5–520.5 | 119.6–115.3 |
| 8 | 01000 | 526.9–545.9 | 113.9–109.9 |
| 9 | 01001 | 552.2–571.3 | 108.6–105.0 |
| 10 | 01010 | 577.6–596.7 | 103.9–100.6 |
| 11 | 01011 | 603.0–622.1 | 99.5–96.5 |
| 12 | 01100 | 628.4–647.5 | 95.5–92.7 |
| 13 | 01101 | 653.8–672.9 | 91.8–89.2 |
| 14 | 01110 | 679.2–698.2 | 88.3–85.9 |
| 15 | 01111 | 704.6–723.6 | 85.2–82.9 |
| 16 | 10000 | 730.0–749.0 | 82.2–80.1 |
| 17 | 10001 | 755.4–774.4 | 79.4–77.5 |
| 18 | 10010 | 780.8–799.8 | 76.8–75.0 |
| 19 | 10011 | 806.2–825.2 | 74.4–72.7 |
| 20 | 10100 | 831.5–850.6 | 72.2–70.5 |
| 21 | 10101 | 856.9–876.0 | 70.0–68.5 |
| 22 | 10110 | 882.3–901.4 | 68.0–66.6 |
| 23 | 10111 | 907.7–926.8 | 66.1–64.7 |
| 24 | 11000 | 933.1–952.1 | 64.3–63.0 |
| 25 | 11001 | 958.5–977.5 | 62.6–61.4 |
| 26 | 11010 | 983.9–1002.9 | 61.0–59.8 |
| 27 | 11011 | 1009.3–1028.3 | 59.4–58.3 |
| 28 | 11100 | 1034.7–1053.7 | 58.0–56.9 |
| 29 | 11101 | 1060.1–1079.1 | 56.6–55.6 |
| 30 | 11110 | 1085.4–1104.5 | 55.3–54.3 |
| 31 | 11111 | 1110.8–1129.9 | 54.0–53.1 |

In addition to the event type and cycle timing information presently included in the pacing event data record 90, additional bits are included as part of each pacing event data record 90, namely, variables A through Z as depicted in FIG. 3. Preferably, parametric data such as P-wave and R-wave amplitudes are included in the pacing event data record 90 as "variable A" 96 and "variable B" 97, respectively. The P-wave and R-wave amplitudes may be stored, for example, as six bit sequences representing a given range of values. As with the other data entries in the pacing event data record 90, the appropriate bit sequence corresponding to the measured amplitudes is generated from a look-up table (not shown). Additional parametric data such as atrial lead impedance, ventricle lead impedance, physiological sensor readings, pacemaker state information, clocking information representative of atrial-ventricle (AV) time intervals and/or ventricle-atrial time intervals can also be incorporated into the alternate variable locations 98 and 99 (variable C through variable Z) of the pacing event data record 90.

Figure 4:
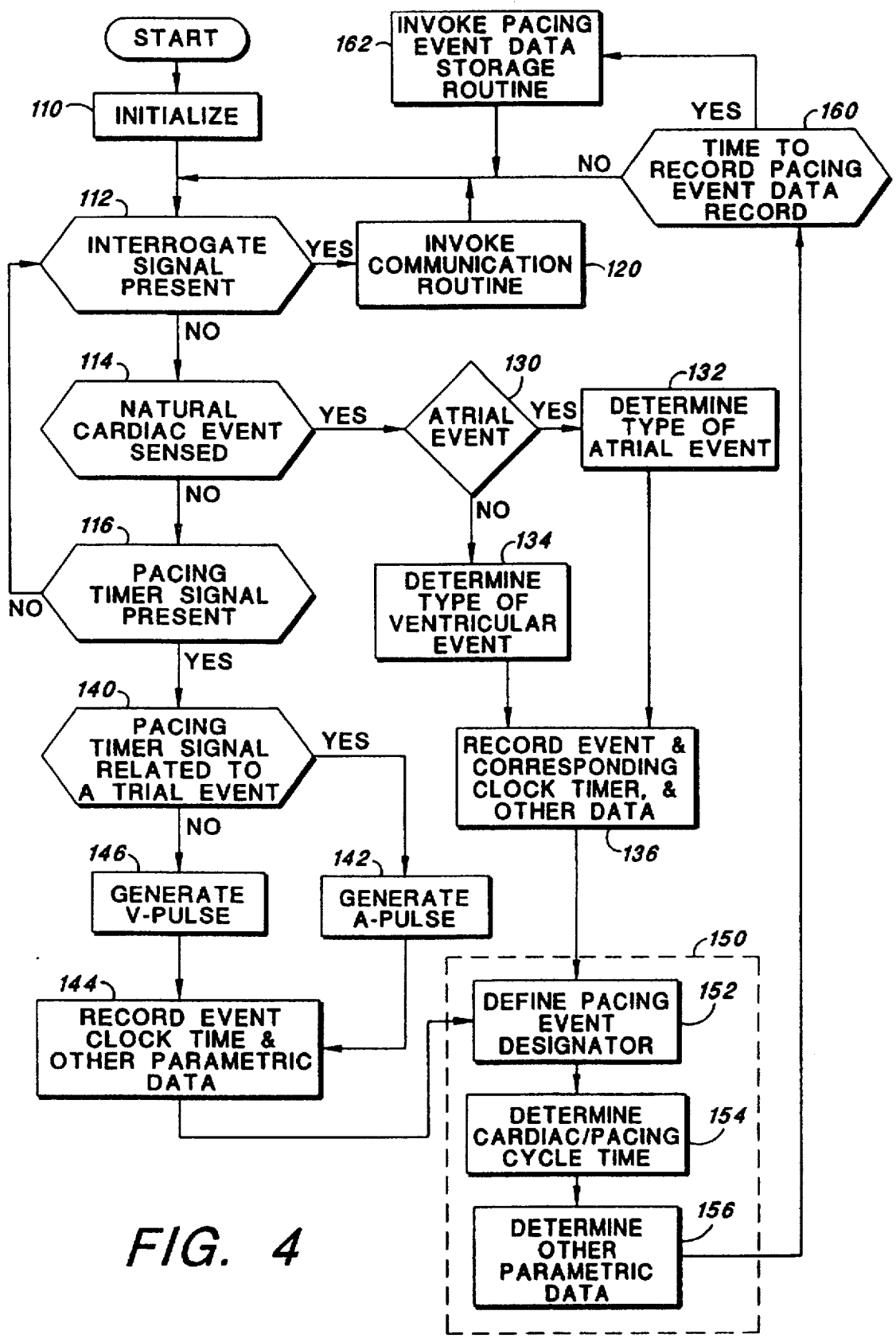
FIG. 4 is a simplified functional flowchart depicting the manner in which pacing event data records are typically generated and recorded by an implanted pacemaker.
Figure 5:
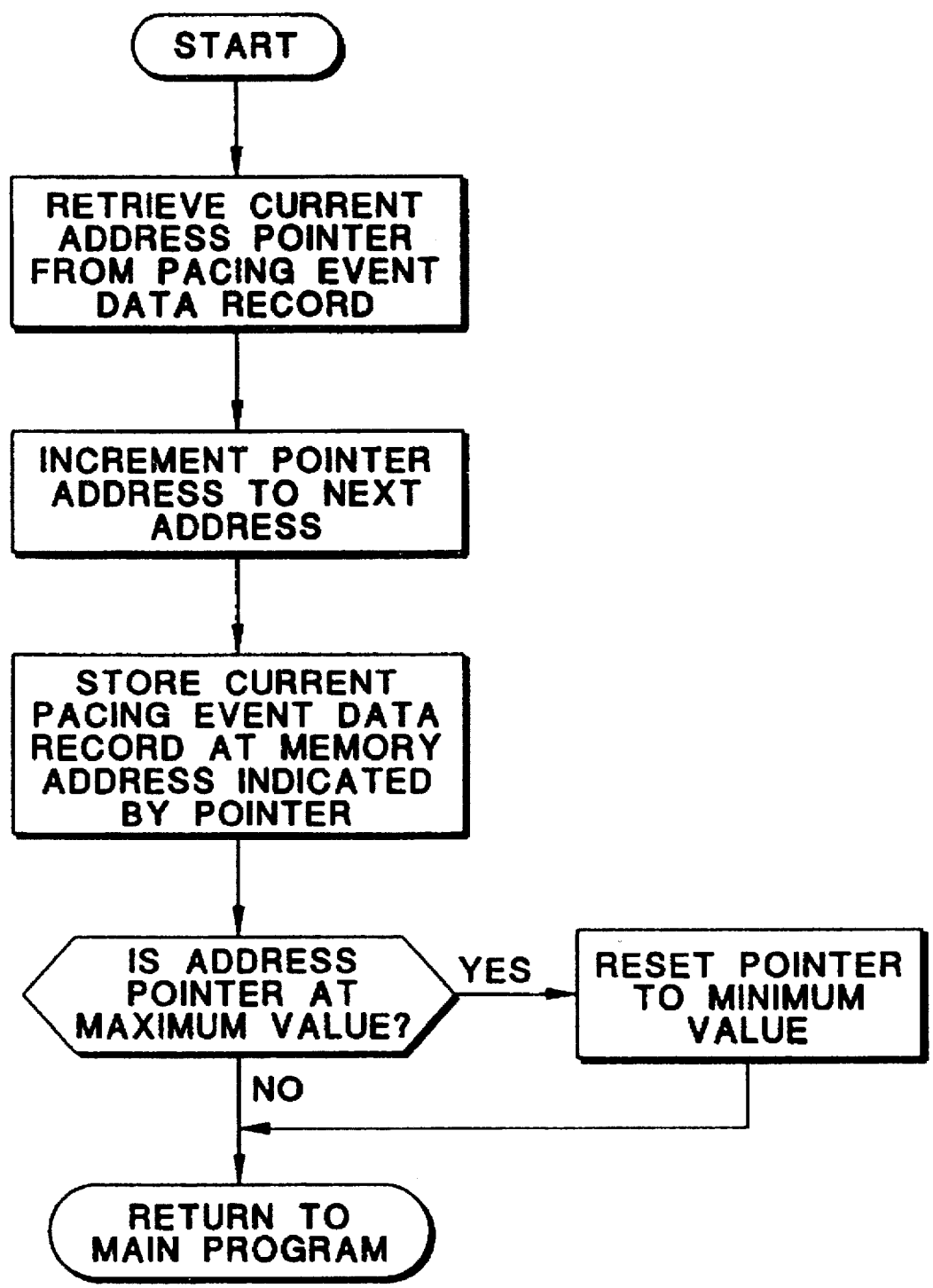
FIG. 5 is a simplified functional flowchart depicting one manner in which pacing event data records may be stored in a buffer memory of the pacemaker.

Turning next to FIGS. 4 and 5, there is shown a simplified flowchart that depicts one manner in which the implanted pacemaker 12 may collect the pacing event data records 90 and store such records in the buffer memory 92 of the pacemaker 12. In FIGS. 4 and 5, each main program step executed by the pacemaker data collection process is referred to as a "block", with a reference numeral being assigned to each block for identification purposes. Referring to FIG. 4, a first step of the process is to perform initialization steps, such as initializing various variables, clearing or setting registers, and the like (block 110). Once the initialization has occurred, a determination is made as to whether an "interrogate" signal is present (block 112). An "interrogate" signal, for example, can originate from the programmer device and be telemetered to the pacemaker processor.

Alternatively, an interrogate signal may be generated within the pacemaker at a prescribed rate, or upon the occurrence of certain events. The "interrogate" signal typically indicates that either a programming change to the pacemaker is required or the collected data is to be downloaded to the programmer device. If an "interrogate" signal is not present then a determination is then made as to whether a natural cardiac event, such as an R-wave or a P-wave has been sensed (block 114). If not, then a further determination is made as to whether a pacing timer signal is present (block 116). A pacing timer signal originates from the pacemaker circuitry and/or pacemaker processor when a defined timing interval has exceeded a prescribed maximum duration. If a pacing timer signal is not present, then the program control loops back to block 112, and the process continues. In other words, the main branch of the program for the internal processor of the pacemaker, or equivalent state logic circuitry, essentially waits for either a pacing signal to be received from the pacemaker circuitry, an "interrogate" signal received from the programmer device, or a naturally occurring cardiac signal sensed by the pacemaker. As soon as one of these signals are present, the program executes the appropriate routine as more fully described below.

If an "interrogate" signal is received (block 112), then that indicates the telemetry head of the external programmer is in place, and an appropriate communication routine is invoked (block 120) to establish the telemetry link and to allow data to be transferred from the pacemaker, or to allow control parameters to be transferred to the pacemaker in order to program the pacemaker.

If a natural cardiac signal is sensed (block 114), a determination is then made as to whether the sensed signal is related to an atrial event (block 130). If so, then a further determination is made as to the type of atrial event (block 132), which determination is easily made by monitoring the operating state of the pacemaker. If the event is not an atrial event (block 130), then that indicates the event must be a ventricular event, and an appropriate ventricular event type is defined (block 134). The occurrence of such events is recorded (block 136) in a temporary buffer or register. Also recorded is a corresponding indication of the cardiac/pacing cycle associated with such event. The cardiac/pacing cycle is determined or measured by an internal clock or timer (not shown), and provides an indication of the current pacing rates. Typically, the internal clock or timer measures the time period between successive ventricular events, V-pulses or R-waves, or may be configured to measure the time between successive atrial events, P-waves or A-pulses. Another clock or timer may also be used to measure the time interval between an atrial event and the successive ventricular event (AV interval), or to measure the time interval between an ventricular event and the following atrial event (VA interval).

If a pacing timer signal is received (block 116), then a determination is made as to the type of pacing timer signal (block 140). If the signal relates to an atrial event, then an A-pulse is generated (block 142) by the pacemaker and recorded (block 144) in a temporary buffer or register. If the pacing timer signal is not related to an atrial event, then a V-pulse is generated (block 146) by the pacemaker and also recorded in a temporary buffer or register (block 144). In this manner, one or more temporary buffers or registers keeps a temporary record of the last n events that have occurred, where n is at least two, including the pacing/cardiac cycle time and appropriate interval times associated with such events. Other parametric values associated with the particular atrial or ventricular event are also stored in each temporary record (block 144).

From the information held in the temporary buffer or registers, as above described, a pacing event data record 90 is produced (block 150), which record includes a plurality of data fields as shown in FIG. 3. The Pacing Event Designator is defined as a first field of an pacing event data record (block 152). See Table 1 for a definition of the Event Designators that are used. Also, the Cycle Time associated with the pacing event data record is defined as a second field (block 154). See Table 2 for a definition of the Cycle Times and corresponding values of a look-up table that are used. A third field, identified as variable A in FIG. 3, is reserved for parametric data such as the amplitude of the signal associated with the atrial event (A-pulse or P wave). Another field, identified as variable B in FIG. 3, is reserved for parametric data such as the amplitude of the signal associated with the ventricular event (V-pulse or R wave). These other variables can be determined and stored in the temporary registers and subsequently incorporated into the pacing event data records (block 156). These fields are particularly useful for information such as timing intervals, physiological sensor data, pacemaker state information and other parametric data.

As disclosed above, it is seen that pacing events are recorded in sequence as they occur and are stored to the buffer memory at a specified sampling rate. If it is time to update the pacing event data record (block 160), as determined by the programmed Sampling Rate, then the pacing event data record 90 it is stored in the buffer memory 92. If it is not time to update the Event Record (block 160), then the program loops back to the main wait loop (blocks 112, 114), and the information or data stored in the temporary resisters will be replaced with the next set of information and data that is associated with the next pacing cycle. The pacing event data records 90 are stored in the pacemaker memory 92 in such a way that they can be retrieved in the same order or in the reverse order in which they were stored. The process of storing the pacing event data records is more clearly depicted in FIG. 5.

As shown in FIG. 5, if it is time to update the pacing event data record, then an address pointer is retrieved (block 170), or otherwise accessed, from a designated memory location and is incremented by an appropriate value (block 172), with the increment being dependent on the defined length pacing event data records. The current pacing event data record is then stored at the address indicated by the address pointer (block 174). A determination is then made if the pointer is at its maximum value (block 176), and if so, the pointer is reset to its minimum value (block 178). Thus, the pacing event data memory of the pacemaker is generally accessed as a "continuous" type buffer. This has the effect of continuously overwriting the oldest pacing event data record in the allotted memory with the newest pacing event data record, provided the program is not suspended due to the presence of an "interrogate" signal from the programmer or other designated "interrupt" signal. After the pacing event data record has been stored the program returns to the main pacemaker data collection program (block 180).

As with any programmable implantable pacing device, it is the programmed parameters of the pacemaker that influence the event types, cycle times and additional parametric data that are recorded. The interaction between the pacemaker timers, the maximum allowable timing intervals, and the intrinsic activity of the patient's heart ultimately determine the device behavior, and thus the pacing event data records collected.

The pacing event data records are downloaded from the pacemaker to the programmer using any suitable communication routine (Block 120, FIG. 4). The details of such communication routine are not important to the present invention. Any suitable communication routine that transfers the pacing event data records from the pacemaker to the programmer, as is known in the art, or as is yet to be developed in the art, may be used. All that matters for purposes of the present invention is that the event data records, recorded by the pacemaker and stored in the memory of the pacemaker, eventually find their way into the memory of the programmer. Numerous data transfer techniques are known in the art that may be used for this purpose. See, e.g., U.S. Pat. No. 4,944,299 (Silvian), incorporated herein by reference.

The present invention relates primarily to the analysis and display of an Event Record of an implantable pacemaker using a programmer device. By using the APS-II programmer processing circuits and memory, or equivalent, as controlled by an appropriate analysis and display routine or program stored in the program cartridge, the downloaded pacing event data records may be processed and stored in an Event Record format for subsequent displaying and printing in simple and comprehensible graphical formats. The preferred Event Record represents an entire sequence of downloaded pacing event data records together with dynamic statistical and summary information relating thereto.

One of the important features of the invention is that the pacing event data records that make up the Event Record are time logged by the APS-II programmer as they are downloaded from the pacemaker. That is, the pacing event data record itself only includes an event type indicator, a cycle time indicator and other prescribed parametric data. However, because the pacing event data records are recorded at a known sampling rate, and because the pacing event data records are always current, the APS-II processing circuits, which include a real time clock, can mark the time of the most recent pacing event data record, and then work backwards in time, assigning each pacing event data record an appropriate time of occurrence.

Once each pacing event data record is assigned a time of occurrence, the pacing event data records contained in the Event Record are grouped or arranged by events into time slots consistent with the available time scale selections, as more fully described below. The original parametric data together with the processed statistical information are also stored or arranged into time slots consistent with the available time scale selections.

Figure 6:
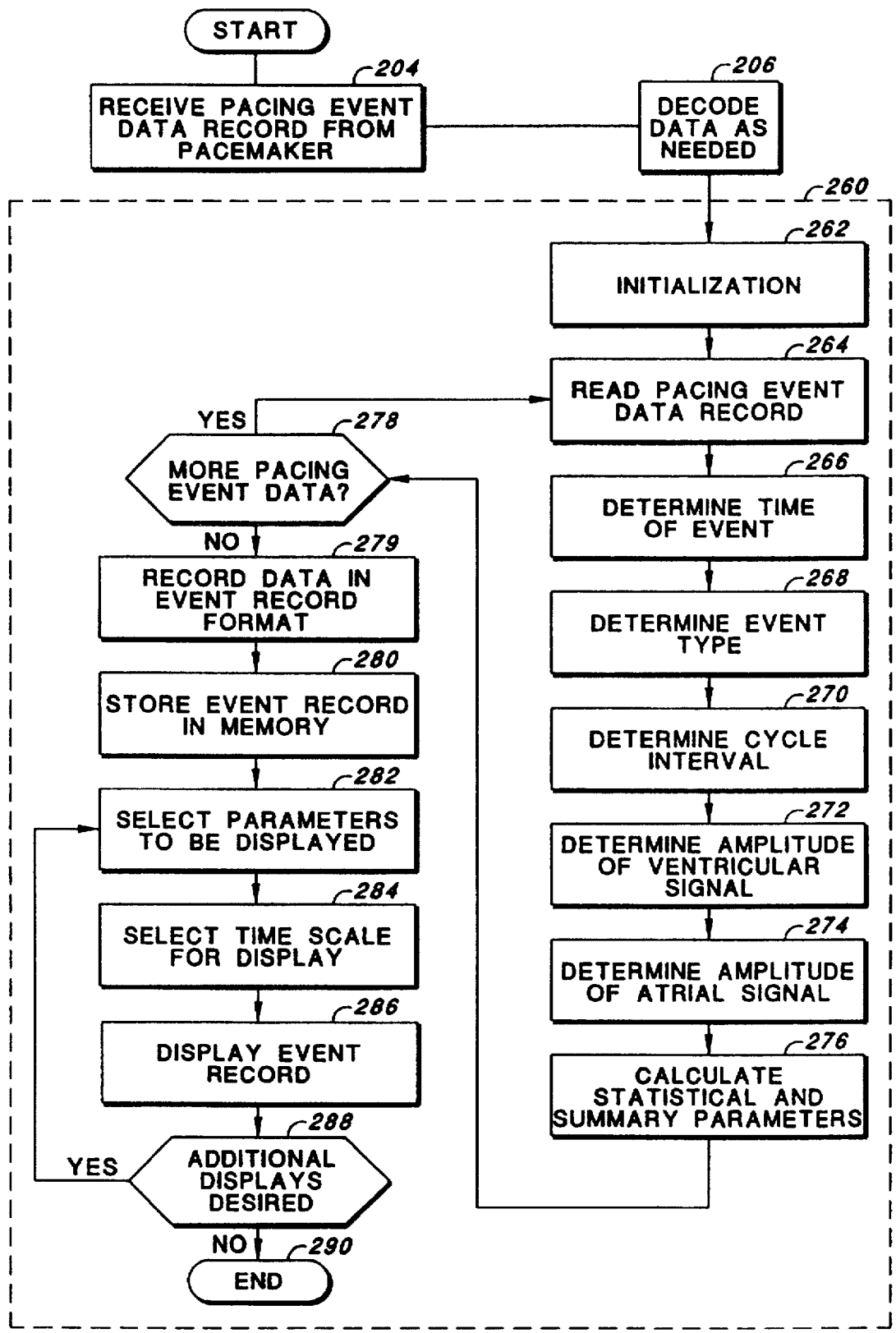
FIG. 6 is a somewhat more detailed flowchart depicting the manner in which the pacing event data are processed, stored, and subsequently displayed as an Event Record in accordance with the present invention.

As seen in FIG. 6, the invention includes an Event Record analysis and display routine or program. This analysis and display routine provides for the receipt of pacing event data records downloaded from the pacemaker (block 204). Once downloaded, the data records are decoded (block 206). The pacing event data records are then analyzed and displayed by the APS-II programmer processing circuits (block 260). Preferably, the analysis and display of the pacing event data records involves an initialization step (block 262) which may include steps such as ascertaining the sample interval used in collecting the data, reading the real-time clock, clearing or setting registers, and the like. Next, an individual pacing event data record is read (block 264) and the estimated time of the event is determined (block 266), including the year, month, day, hour, minute and second, as described above. The Event Type is then determined (block 268) by processing the bit sequence in field 1 of the current pacing event data record. A determination of the appropriate Cycle Interval is then made (block 270) by processing the bit sequence in field two. Similarly, by processing the data contained in fields 3 and 4, the "Amplitude of the Ventricular Signal" and "Amplitude of the Atrial Signal" are determined (blocks 272 and 274). The remaining statistical parameters are then updated based on the information contained in the current pacing event data record (block 276). After the statistical parameters have been updated (block 276), the program then determines if there is another pacing event data record that needs to be read (block 278). If so, the program loops back to block 264 and repeats the above described process until all the pacing event data records have been read and processed. After all the pacing event data records have been processed into an Event Record format, the program records the parameters in an Event Record format (block 279) and stores the Event Record in a memory location of the APS-II programmer (block 280).

The APS-II processing program then awaits selections by the user of one or more parameters contained in the Event Record to be displayed in a graphical format (block 282), or absent such selection, defaults to a preset parameter set. Likewise, the APS-II processing program then awaits another selection by the user of a time scale to be used as the abscissa for the graph to be displayed (block 284), or defaults to a preset time selection. As described herein, the selections are made from various selection tables presented to the user. Based on the selections of the user, the program proceeds to generate and display electronic images on the display screen of the APS-II programmer corresponding to a graph of the selected parameters according to the time scale selected (block 286). After the display is produced, the program determines whether the user has selected alternative commands (block 288) which ends the analysis and display routine (block 290). Alternatively, the program or routine loops back to block 282 and the user is prompted to make new selections of the Event Record parameters or time scales.

The Event Record includes numerous data fields contained within a relational data structure (i.e. database). Preferably, the Event Record contains, for example, the following static fields extracted from the pacing event data records: Event Designation; Year; Month; Day; Hour; Minute; Amplitude of Ventricular Signal; Amplitude of Atrial Signal. The Event Record may also contain a plurality of statistical and summary fields that are dynamically calculated for each of the prescribed time scales (month, day, hour, etc.) as the data is being processed. These dynamic fields of the Event Record may include: Average Sensed Heart Rate; Average Pacing Heart Rate; Maximum Amplitude of Ventricular Capture Threshold Signal; Minimum Amplitude of Ventricular Capture Threshold Signal; Median Amplitude of Ventricular Signal; Standard Deviation of the Ventricular Capture Threshold Signal; Maximum Amplitude of Atrial Capture Threshold Signal; Minimum Amplitude of Atrial Capture Threshold Signal; Median Amplitude of Atrial Capture Threshold Signal; Standard Deviation of Atrial Capture Threshold Signal; Total P-Waves; Total R-waves; Total A-pulses;-Total V-pulses; Total PVE's; Percent Ventricular Pacing Events; Percent Ventricular Inhibition Events; Percent Atrial Pacing Events; Percent Atrial Inhibition Events; Total Ventricular Loss of Capture Events; and Total Atrial Loss of Capture Events. Additional parameters, both static and dynamic, may be added to the Event Record if required or desired by the user.

It is noted that the data analysis functions carried out by the APS-II programmer, as far as computing statistical or summary information relative to the pacing event data records, is straightforward, and may be readily programmed by those of skill in the art. For example, average parametric values, minimum, maximum and median parametric values, standard deviations, ratios, and frequency of occurrence are simple parameters to calculate for any given time scale, and the manner in which to calculate such parameters is well known in the art. However, the manner and format in which the Event Record (i.e. pacing event parametric data) is displayed can have a significant impact on how useful the data is to the physician or other medical personnel in understanding the operation of the pacemaker for a particular patient.

To present the data to the user, the processed Event Record is displayed in a graphical format using a selected time scale as the abscissa and selected parameters as the ordinate of the graph. Optionally, the graphical display can be printed by the APS-II. To illustrate the manner and various formats in which the Event Record data may be displayed, reference is next made to FIG. 7 where there is shown a screen display flow chart that maps the relationship between the main screen displays generated by the external APS-II programmer as it displays the Event Record in various formats. When the APS-II programmer is first turned on, a main menu screen 310 is displayed. This Main Menu screen 310 allows the user to select "Interrogate" as a command in order to establish the appropriate telemetry link with the pacemaker by touching an interrogate icon button 313. In response to selecting "Interrogate", a telemetry link is established between the APS-II programmer and the pacemaker. The pacemaker downloads identifying information about the pacemaker, such as its model number and serial number, as well as the current set of programmed parameters that reside in the pacemaker. Such information is displayed in a Data Display screen 312.

Several icon "buttons" are displayed along one side of the Data Display screen 312 that provide the user additional options relative to using the APS-II to interrogate and program the pacemaker. One of these "buttons", for example, may be a "Sensor Parameter" button 314. If the "Sensor Parameter" button 314 is pressed (meaning if the icon representing the button is touched), then a Sensor Parameter screen 316 is displayed, as seen best in FIGS. 8–11. The Sensor Parameter screen 316 may include several additional "buttons" that provide the user with still further options as are described, e.g., in more detail in U.S. Pat. No. 5,309,919 entitled METHOD AND SYSTEM FOR RECORDING, REPORTING, AND DISPLAYING THE DISTRIBUTION OF PACING EVENTS OVER TIME AND FOR USING THE SAME TO OPTIMIZE PROGRAMMING; U.S. Pat. No. 5,431,691 entitled METHOD AND SYSTEM FOR RECORDING, AND REPORTING A SEQUENTIAL SERIES OF PACING EVENTS; and U.S. Pat. No. 5,292,341 entitled METHOD AND SYSTEM FOR AUTOMATICALLY DETERMINING AND ADJUSTING THE SENSOR PARAMETERS OF A RATE-RESPONSIVE PACEMAKER; all of which are incorporated herein by reference.

In the disclosed embodiment, one of the buttons that is present in both the Data Display screen 312 as well as the Sensor Parameter screen 316 includes a "Return" button 317 which, when pressed, causes the previous screen to be displayed. Another button available to the user is an "Event Record" button 318. If the "Event Record" button 318 on the Sensor Parameter screen 316 is pressed, then an Event Record screen 320 is displayed as seen best in FIGS. 8–11. The Event Record screen 320 includes a graphical display area 322 and two parameter selection tables 324, 326 and a plurality of icon "buttons" (331 through 339).

The first parameter selection table 324 is in a menu format that identifies a plurality of parameters and associated parametric data that can be displayed in the Event Record screen 320. The second parameter selection table 326 provides a menu of available time scales that can be used to display the selected parameter. The Event Record graphical display area 322 is an essentially two dimensional graph that includes the selected parameters and associated parametric data along the vertical axis, and the selected time scale along the horizontal axis.

Representative illustrations of the parameter selection tables 324 and 326 are depicted, respectively, in Table 3 and Table 4 below. Note that in Table 3 and Table 4, a cursor is moved up and down the left side of the table to select the desired parameter. Thus, in the Table 3 example below, the cursor is placed next to the "DAY" parameter in order to select "DAY", while in the Table 4 example below, the cursor is placed next to the "AVERAGE PACING RATE" parameter in order to select the average pacing rate as the parameter. The values of the parameters shown in the right column of Table 4 are representative of typical parameter values.

TABLE 3

(Example of Parameter Selection Table 324)

| ABSCISSA |
|---|
| YEAR |
| MONTH |
| → DAY |
| HOUR |
| MINUTE |
| SAMPLE |

TABLE 4

(Example of Parameter Selection Table 326)

| ORDINATE | VALUE |
|---|---|
| AVERAGE SENSED RATE | 65 BPM |
| → AVERAGE PACING RATE | 72 PPM |
| ATRIAL INHIBITION | 21% 19,656 PW |
| ATRIAL PACING | 79% 73,944 AP |
| VENTRICULAR INHIBITION | 97% 100,570 RW |
| VENTRICULAR PACING | 3% 3,110 VP |
| ATRIAL CAPTURE THRESHOLD | 1.7 V MIN |
| | 2.0 V AVG |
| | 3.5 V MAX |
| ATRIAL LOSS OF CAPTURE | 2 Times |
| STANDARD DEVIATION: ATRIAL CAP THRESHOLD | 0.12 V |
| VENTRICULAR CAPTURE THRESHOLD | 1.4 V MIN |
| | 1.8 V AVG |
| | 2.1 V MAX |
| VENTRICULAR LOSS OF CAPTURE | 21 Times |
| STANDARD DEVIATION: VENT CAP THRESHOLD | 0.15 V |
| NO. OF AUTO DDD-DDI CHANGES | 5 Times |
| AVERAGE ATRIAL TACHYCARDIA RATE | 210 BPM |
| NO. OF PREMATURE ATRIAL EVENTS | 17 |
| NO. OF PREMATURE VENTRICULAR EVENTS | 2 |
| [OTHER PARAMETERS AS DESIRED] | |
| - - - | — |
| - - - | — |
| - - - | — |

Figure 7:
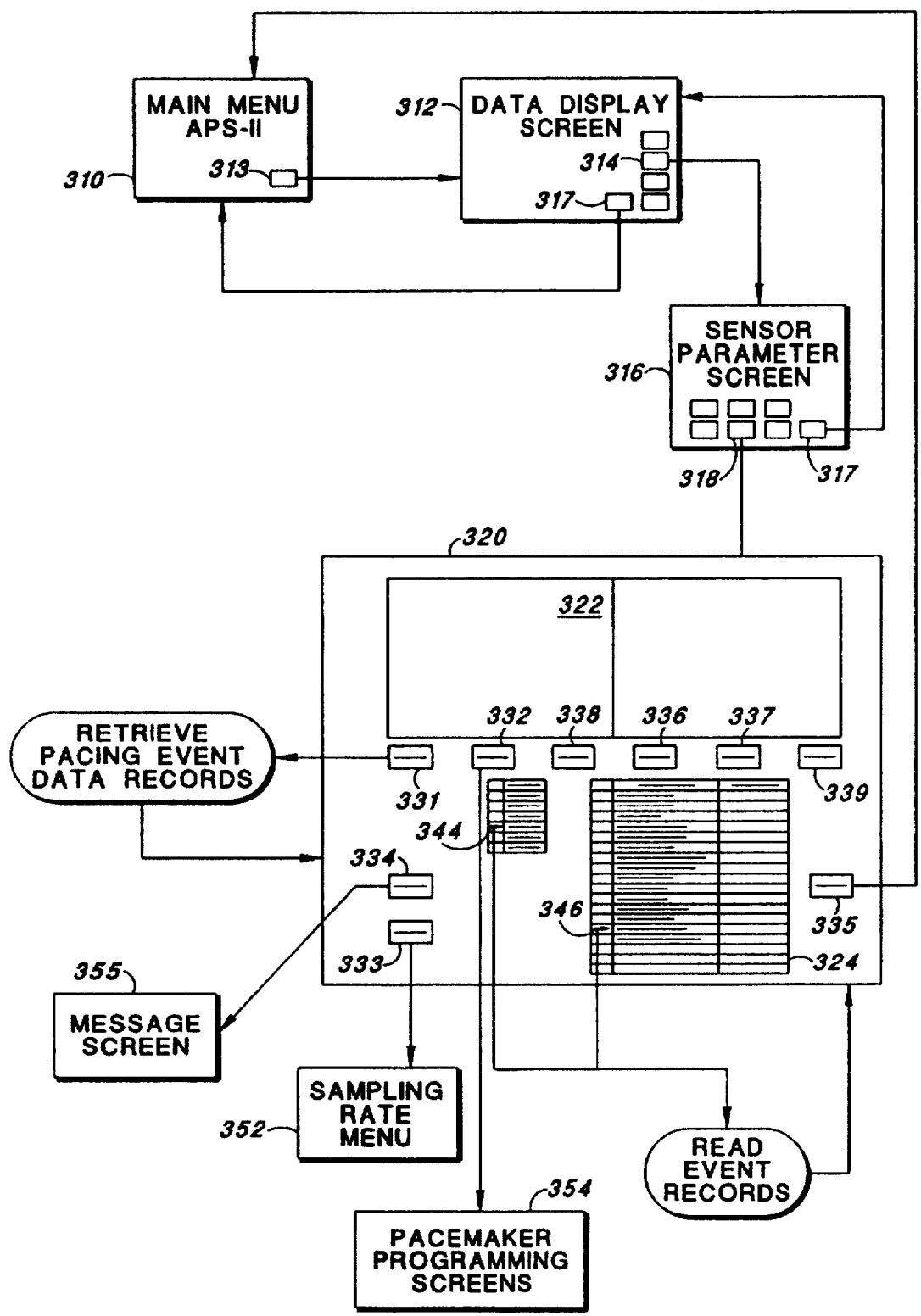
FIG. 7 is a screen display flow chart that maps the relationship between the screen displays generated by the external programmer as it displays the parametric data for an Event Record over a prescribed period of time.
Figure 8:
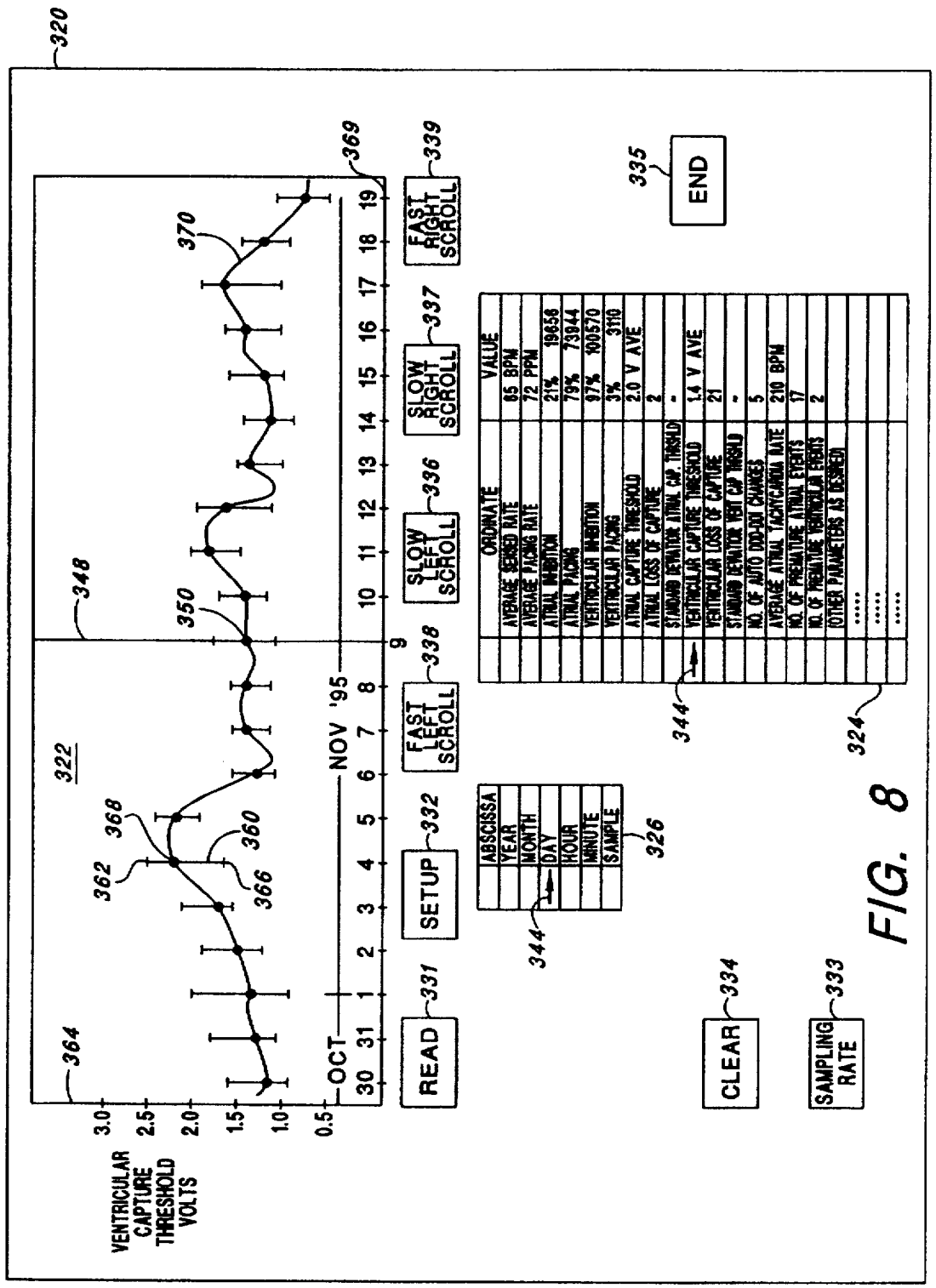
FIG. 8 is a typical Event Record screen as displayed on the external programmer with a selected time scale of "Day" and a selected parameter of Ventricular Capture Threshold being displayed.

Referring to FIGS. 8–11, as well as Table 3 and Table 4, the user selects a time scale in which the parametric data is to be displayed by positioning a cursor 344 or highlighted bar on the desired time scale value within the second parameter selection table 326. The available time scale selections in the disclosed embodiment include: (1) Year; (2) Month; (3) Day; (4) Hour; (5) Minute; and (6) Sample. The selection "Sample" corresponds to the sample rate at which the pacing event data records were originally collected e.g. 1.6 seconds or 26 seconds. Different time scales are selected by simply touching or indicating a different selection. The user also selects the parameter or parameters to be displayed along the vertical axis by selecting the desired parameters from the parameter selection table 324 with a pointing cursor 346. As seen in FIGS. 7 and 8, the choice of parameters to be displayed is made from a relatively large selection, but advantageously, the presentation of the graphical data is done in a consistent, and easily comprehensible format for all the available parameters. Additional or different parameters are indicated by simply selecting and/or deselecting the various parameters using the pointing cursor.

A series of icon "buttons" also appear within the Event Record screen 320. These buttons include a "Read" button 331, "Setup" button 332, "Sampling Rate" button 333, "Clear" button 334, "End" button 335, "Slow Left Scroll" button 336, "Slow Right Scroll" button 337, "Fast Left Scroll" button 338, and "Fast Right Scroll" button 339.

If pacing event data records have not been downloaded from the pacemaker, then the "Read" button 331 may be pressed to effectuate such reading. Depressing the "Read" button 331 forwards a "read" command signal to the pacemaker processor. As described above, the pacemaker proceeds to download the data resident in the buffer memory to the programmer device where it is processed and stored. After the pacing event data records have been read from the pacemaker buffer memory, processed, and stored into the Event Record format then such data will be reflected in the Event Record screen 320.

Depending on the time scale selected by the user, all of the Event Record data for the selected parameter may or may not fit within display area 322 on the Event Record screen 320. The graphical display of the selected parameter can advantageously be scrolled left or right along the abscissa to allow a specific time period within the Event Record to be displayed. Also seen in FIG. 8, a broad line 348 or other highlighted or boldedline, appears in the center of the Event Record screen 320. This broad light line 348 provides an identification marker 350 for marking a single point (i.e., reference point or base-line point) of the graphical display. The identification marker 350 is particular useful during scrolling and otherwise examining the data.

Scrolling of the graphical display is accomplished by depressing the "Slow Left Scroll" button 336, "slow Right Scroll" button 337, "Fast Left Scroll" button 338, or "Fast Right Scroll" button 339. Scrolling "left" causes the display to simulate a move backwards in time at the indicated speed consistent with the selected time scale. Scrolling "right", on the other hand, causes the graphical display to simulate a move forward in time at the indicated speed ("Fast" or "Slow"). For example, if the selected time scale is "Day" and parametric data for days 1–20 are currently displayed, when the "Slow Right Scroll" button 337 is depressed, the Event Record data corresponding to the "day 21" will be included in the display while the Event Record data corresponding to "day 1" will be removed from the display. Further, when the display is scrolled in either direction the broad light line 348 remains fixed in the center of the screen, thus identifying a new point.

An additional feature of the present embodiment is that the actual parametric data values corresponding to the point at which the identification marker is located on the displayed graph are displayed in a tabular format as part of the parameter selection table 324. Thus, as the graphical display is scrolled the parametric data values displayed in the parameter selection table 324 change to allow the user to closely examine any aspect of the Event Record.

Turning again to FIGS. 7 and 8, if the "Sampling Rate" button 333 is depressed, a "Sample Rate" command signal is generated and passed to the pacemaker programmer. The display then presents the user with a table or menu 352 of sampling rate choices including: (1) Every Event; (2) 1.6 Seconds; (3) 26 Seconds; and (4) Other. After the user makes a selection, the appropriate code is transmitted to the pacemaker where it is stored in a designated portion of the pacemaker memory.

If the "Setup" button 332 is depressed, then a "program" command signal is generated and forwarded to the pacemaker which initiates various routines and corresponding displays 354 to program the pacemaker. On the other hand, if the "Clear" button 334 is pressed, a "clear" command signal is generated and forwarded to the pacemaker which, after appropriate confirmation, proceeds to clear the resident data from the memory buffer. Finally, if the "End" button 335 is depressed, a "termination" command signal is generated and passed to the pacemaker thereby halting the pacemaker communication routine and the APS-II returns to the Main Menu screen display 310 until the next "Interrogate" command is given to re-establish the telemetry link with the pacemaker. The present embodiment of the invention also contemplates additional buttons to activate other program options such as printing and transferring the data.

Referring again to FIG. 8, a typical Event Record screen 320 is shown. The screen is displayed using the APS-II external programmer assuming a time scale of "Day" has been selected. The selected parameter to be displayed is the Ventricular Capture Threshold. Clearly, more than one pacing event is sampled in any given 24 hours, the multiple selected parameters and corresponding parametric values of the multiple events are thus depicted as a vertical line 360 at each indicated day. The top 362 of the vertical line is positioned relative to the vertical scale 364 to represent the maximum amplitude of the ventricular Capture Threshold signal that occurs within each day. The bottom 366 of the vertical line is similarly positioned to represent the minimum amplitude of the ventricular Capture Threshold signal that occurs within each day. A data mark 368 represents the value of the average amplitude of the ventricular Capture Threshold signal that occurs within the particular day. A graph 370 is displayed connecting the data marks 368 corresponding to the average values on each day over the course of the 20 or so days displayed along the horizontal axis 369. Alternatively, when multiple parameters are selected, the display can be programmed to present multiple graphs together with an appropriate legend. In either situation, by simply glancing at the Event Record containing the display of multiple parameters in the same time frame, such as is shown in FIG. 8, useful information is presented to the physician in an easy to understand format for use as a diagnostic tool. More importantly, the selected parameters and/or time scales can be quickly and easily adjusted to allow the physician to focus or broaden the ongoing analysis.

Figure 9:
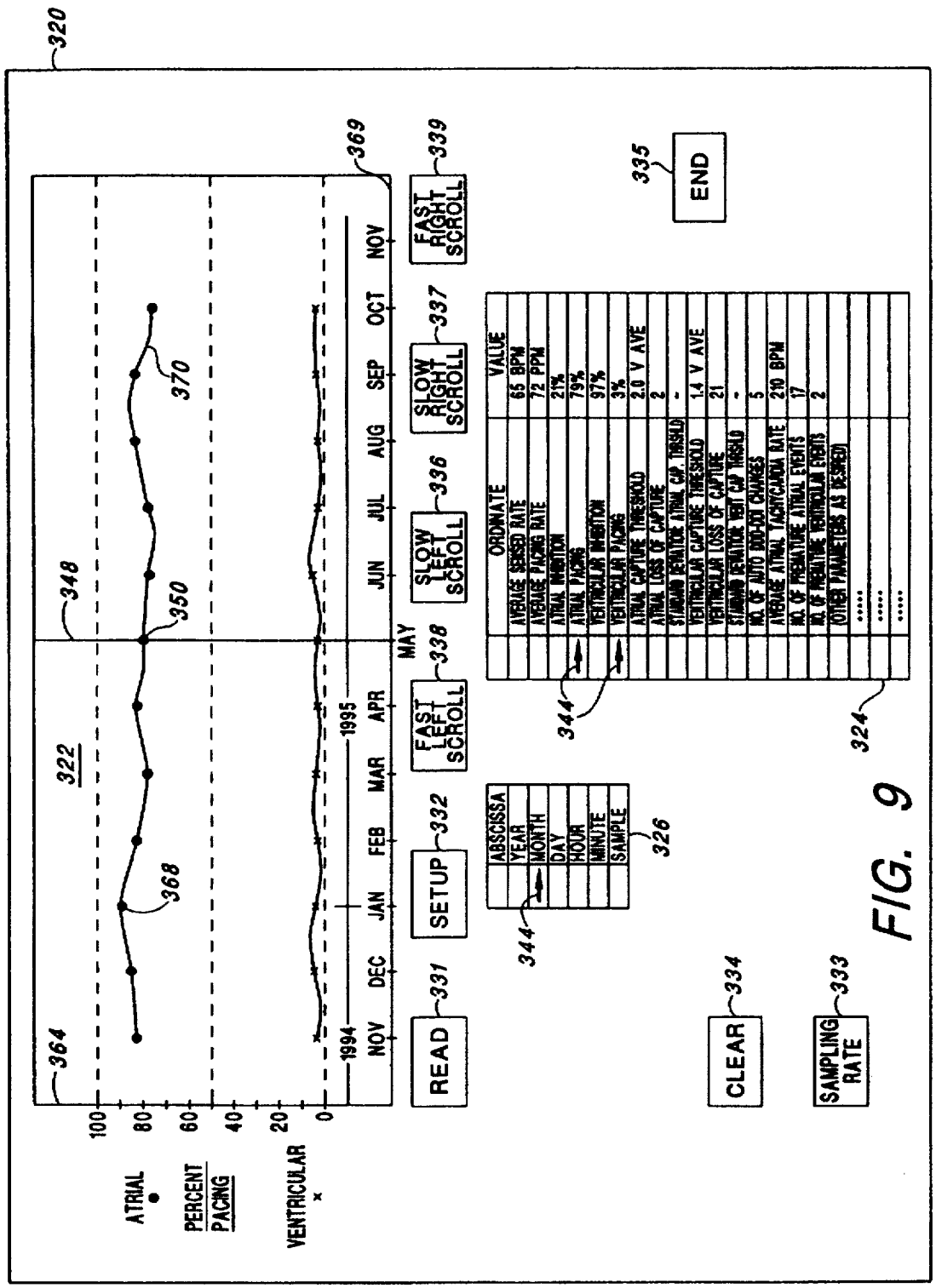
FIG. 9 is a typical Event Record screen as displayed on the external programmer with a selected time scale of "Month" and selected parameters of "Atrial Pacing" and "Ventricle Pacing" being displayed.

Referring next to FIG. 9, another representative Event Record screen 320 is shown as displayed on the APS-II external programmer assuming a time scale of "Month" has been selected, and that the multiple parameters of "Atrial Pacing" and "Ventricle Pacing" have been selected. In many respects, FIG. 9 is very similar to FIG. 8. For example, the parameter selection table 324, the time scale selection table 326, the "icon" buttons, the identification marker 350 and the general format of the parametric data display are the same as in FIG. 8. However, the actual parametric data, the abscissa, and ordinate of the graphical display are quite different. In addition, for the example shown in FIG. 9, the graphical display contains all the available Event Record data for the selected parameter. Hence, it would not be possible to scroll very far to the right or left before reaching the edge of the Event Record.

Figure 10:
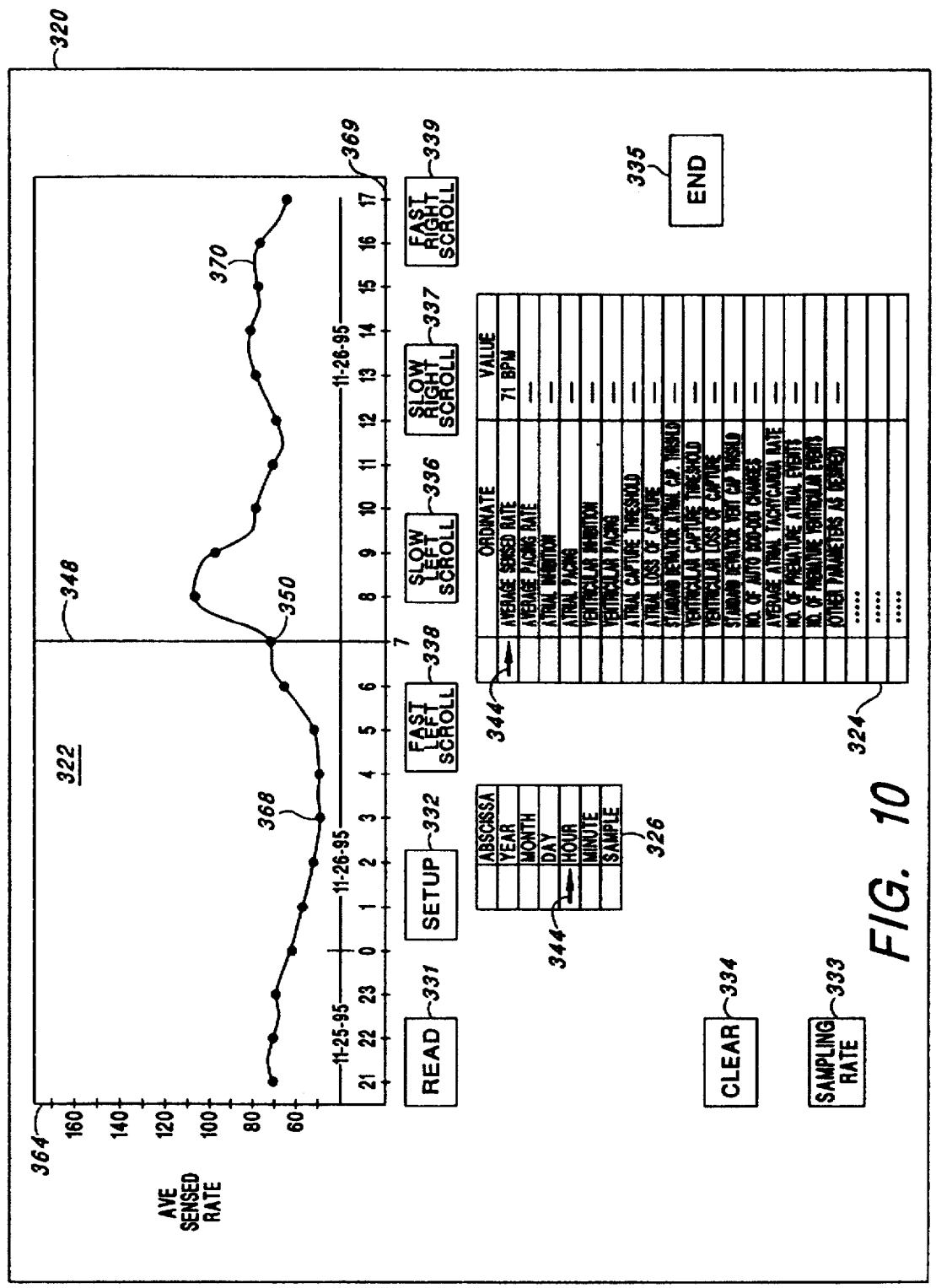
FIG. 10 is a typical Event Record screen as displayed on the external programmer with a selected time scale of "Hour" and a selected parameter of "Averaged Sensed Rate" being displayed.
Figure 11:
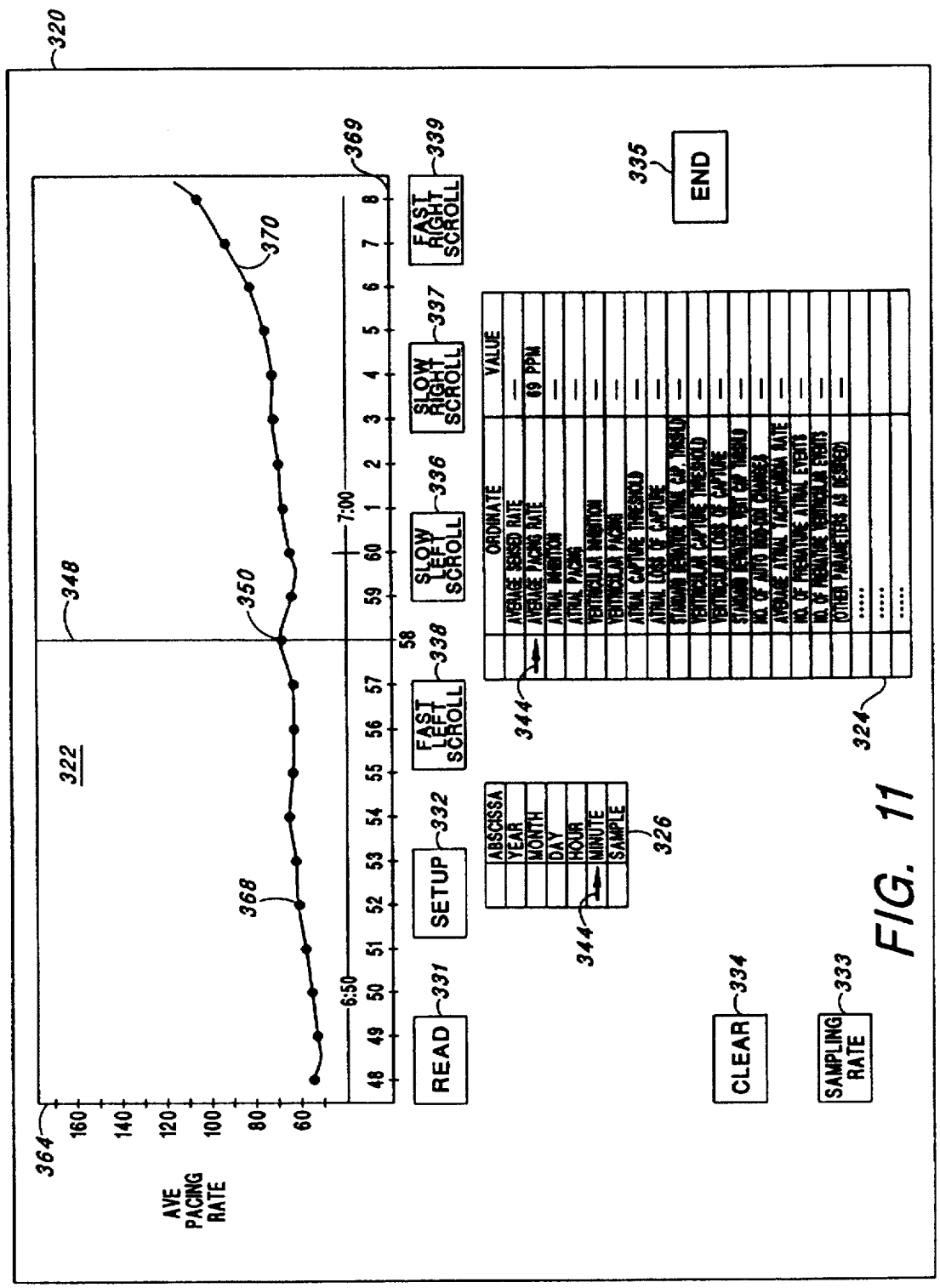
FIG. 11 is a typical Event Record screen as displayed on the external programmer with a selected time scale of "Minute" and a selected parameter of "Average Pacing Rate" being displayed.

Referring next to FIGS. 10 and 11, still other representative Event Record screens 320 are shown as displayed on the APS-II external programmer with a selected time scale of "Hour" and "Minute" respectively. Note that the "Hour" is displayed in a 24 hour format, although this is only exemplary. AM and PM designators could be used with a 12 hour format if desired. The selected parameters illustrated in both FIGS. 10 and 11 are the Averaged Sensed Heart Rate and the Average Paced Heart Rate.

While the invention herein disclosed has been described by means of specific embodiments and applications thereof, numerous modifications and variations could be made thereto by those skilled in the art without departing from the scope of the invention set forth in the claims.

What is claimed is:

1. A method for displaying an event record of an implantable pacemaker using a programmer device, the programmer device having a display screen upon which electronic images may be displayed, the event record including a multiplicity of parameters and corresponding parametric data derived from the operation of the implantable pacemaker over a prescribed period of time, the method comprising the steps of:

downloading pacing event data from the implantable pacemaker to the programmer device;

processing the pacing event data from the implantable pacemaker to produce an event record;

storing the event record in a storage element of the programmer device;

selecting one of the multiplicity of parameters contained in the event record as a selected parameter to be displayed as a graph;

selecting a time scale for an abscissa of the graph to be displayed;

generating and displaying the graph of the parametric data for the selected parameter as an electronic image on the display screen of the programmer device using the selected time scale as the abscissa; and displaying a first table of parameters and corresponding parametric data, the display of the first table being concurrent with the display of the graph, and the first table of parametric data corresponding to a selected point of the graph;

wherein the step of selecting one of the multiplicity of parameters to be displayed in the graph includes selecting the parameter from the first table.

2. The method for displaying the event record of the implantable pacemaker, as set forth in claim 1, further comprising the step of displaying a second table of time scales that may be displayed as the abscissa of the graph, the display of the second table being concurrent with the display of the graph.

3. The method for displaying the event record of the implantable pacemaker, as set forth in claim 2, wherein the step of selecting the time scale for the abscissa of the graph to be displayed further includes selecting the time scale from the second table.

4. The method for displaying the event record of the implantable pacemaker, as set forth in claim 1, wherein the step of selecting one of the multiplicity of parameters contained in the event records as a selected parameter to be displayed as a graph further comprises selecting one or more of the multiplicity of parameters and subsequently generating and displaying one or more graphs of the parametric data for the selected parameters as electronic images on the display screen of the programmer device using the selected time scale as the abscissa in all graphs.

5. The method for displaying the event record of the implantable pacemaker, as set forth in claim 1, further comprising the step of selectively scrolling the graph along the abscissa thereby displaying additional parametric data for the selected parameter as an electronic image on the display screen of the programmer device.

6. The method for displaying the event record of the implantable pacemaker, as set forth in claim 5, wherein the step of selectively scrolling the graph along the abscissa further includes activating a forward scroll button and thereby scrolling the graph at a prescribed rate in a time forward manner, the forward scroll button being located on the programmer device.

7. The method for displaying the event record of the implantable pacemaker, as set forth in claim 5, wherein the step of selectively scrolling the graph along the abscissa further includes activating a backward scroll button and thereby scrolling the graph at a prescribed rate in a time reverse manner, the backward scroll button being located on the programmer device.

8. The method for displaying the event record of the implantable pacemaker, as set forth in claim 5, further comprising the step of marking the selected point of the graph with an identification mark.

9. The method for displaying the event record of the implantable pacemaker, as set forth in claim 8, further including maintaining the identification mark at a fixed location on the display screen as the graph is selectively scrolled along the abscissa.

10. A programmer device for displaying an event record of an implantable pacemaker, the event record including a multiplicity of parameters and corresponding parametric data derived from the operation of the implantable pacemaker over a prescribed period of time, the programmer device comprising:

a display screen upon which electronic images may be displayed;

means for receiving pacing event data from the implantable pacemaker;

means for processing the pacing event data received from the implantable pacemaker to produce event records;

a storage element operatively associated with the processing means and adapted for storing the event records;

a means for selecting one of the multiplicity of parameters contained in the event records as a selected parameter to be displayed in a graphical format;

a means for selecting a time scale representing an abscissa of the graphical format in which the selected parameter is to be displayed;

a means for generating and displaying a graphical representation of the parametric data for the selected parameter as an electronic image on the display screen in the graphical format;

a means for displaying a first table of parameters and corresponding parametric data concurrent with the display of the graphical representation of parametric data, with the first table of parametric data corresponding to a selected point of the graphical representation of parametric data; and a means for identifying the selected parameter displayed in the graphical representation from the first table.

11. The programmer device for displaying the event record of the implantable pacemaker of claim 10, wherein the means for generating and displaying the parametric data further includes a means for displaying a second table of time scales that may be displayed as the abscissa of the graphical representation of the parametric data, the display of the second table being concurrent with the display of the graphical representation of the parametric data.

12. The programmer device for displaying the event record of the implantable pacemaker of claim 11, wherein the means for selecting the time scale for the abscissa of the graph to be displayed further includes a means for identifying the selected time scale from the second table.

13. The programmer device for displaying the event record of the implantable pacemaker of claim 10, further comprising a means for selectively scrolling the graphical representation of the parametric data along the abscissa.

14. The programmer device for displaying the event record of the implantable pacemaker of claim 13, wherein the means for scrolling the graphical representation of the parametric data includes a forward scroll button that when activated causes the graphical representation of the parametric data to scroll along the abscissa in a time forward manner.

15. The programmer device for displaying the event record of the implantable pacemaker of claim 13, wherein the means for scrolling the graphical representation of the parametric data includes a backward scroll button that when activated causes the graphical representation of the parametric data to scroll along the abscissa in a time backward manner.

16. The programmer device for displaying the event record of the implantable pacemaker of claim 13, further including an identification mark as part of the display marking the selected point of the graphical representation of parametric data.

17. The programmer device for displaying the event record of the implantable pacemaker of claim 16, wherein the identification mark remains at a fixed location of the display screen as the graphical representation of the parametric data is selectively scrolled along the abscissa.

18. A method for displaying an event record of an implantable pacemaker using a programmer device, the programmer device having a display screen upon which electronically-generated images may be displayed, the event record including parametric data derived from the operation of the pacemaker over a prescribed period of time, the method comprising the steps of:

downloading the parametric data from the implantable pacemaker to the programmer device;

displaying a first table on the display screen that lists a multiplicity of parameters contained within the parametric data;

displaying a second table on the display screen that lists a plurality of time scales that may be used for examining a selected parameter from the first table;

selecting a parameter from the first table and a time scale from the second table;

generating and displaying a two-dimensional graph of the selected parameter from the first table using the time scale selected from the second table as one of the axes of the two-dimensional graph;

selecting a reference point of the two-dimensional graph;

expanding the first table to include values of the listed parameters corresponding to the selected reference point; and displaying the expanded first table on the display screen of the programmer device along with the two-dimensional graph and the second table.

19. A method for displaying an event record of an implantable pacemaker using a programmer device, the programmer device having a display screen upon which electronic images may be displayed, the event record including a multiplicity of parameters and corresponding parametric data derived from the operation of the implantable pacemaker over a prescribed period of time, the method comprising the steps of:

downloading pacing event data from the implantable pacemaker to the programmer device;

processing the pacing event data from the implantable pacemaker to produce an event record;

storing the event record in a storage element of the programmer device;

selecting one of the multiplicity of parameters contained in the event record as a selected parameter to be displayed as a graph;

selecting one or more time scales for an abscissa of the graph to be displayed; and generating and displaying one or more graphs of the parametric data for the selected parameter as electronic images on the display screen of the programmer device using each of the selected time scales as the abscissa in a single graph.

20. A method for displaying an event record of an implantable pacemaker using a programmer device, the programmer device having a display screen upon which electronic images may be displayed, the event record including a multiplicity of parameters and corresponding parametric data derived from the operation of the implantable pacemaker over a prescribed period of time, the method comprising the steps of:

downloading pacing event data from the implantable pacemaker to the programmer device;

processing the pacing event data from the implantable pacemaker to produce an event record;

storing the event record in a storage element of the programmer device;

selecting one of the multiplicity of parameters contained in the event record as a selected parameter to be displayed as a graph;

selecting a time scale for an abscissa of the graph to be displayed;

generating and displaying the graph of the parametric data for the selected parameter as an electronic image on the display screen of the programmer device using the selected time scale as the abscissa;

displaying a first table of parameters and corresponding parametric data, the display of the first table being concurrent with the display of the graph, and the first table of parametric data corresponding to a selected point of the graph;

selectively scrolling the graph along the abscissa thereby displaying additional parametric data for the selected parameter as an electronic image on the display screen of the programmer device; and marking the selected point of the graph with an identification mark and maintaining the identification mark at a fixed location of the display screen as the graph is selectively scrolled along the abscissa.

21. A method for displaying an event record of an implantable pacemaker using a programmer device, the programmer device having a display screen upon which electronic images may be displayed, the event record including a multiplicity of parameters and corresponding parametric data derived from the operation of the implantable pacemaker over a prescribed period of time, the method comprising the steps of:

downloading pacing event data from the implantable pacemaker to the programmer device;

processing the pacing event data from the implantable pacemaker to produce an event record;

storing the event record in a storage element of the programmer device;

selecting one of the multiplicity of parameters contained in the event record as a selected parameter to be displayed as a graph;

selecting a time scale for an abscissa of the graph to be displayed;

generating and displaying the graph of the parametric data for the selected parameter as an electronic image on the display screen of the programmer device using the selected time scale as the abscissa; and displaying a first table of parameters and corresponding parametric data, the display of the first table being concurrent with the display of the graph, and the first table of parametric data corresponding to a selected point of the graph;

wherein the step of selecting one of the multiplicity of parameters contained in the event records as a selected parameter to be displayed as a graph further comprises selecting one or more of the multiplicity of parameters and subsequently generating and displaying one or more graphs of the parametric data for the selected parameters as electronic images on the display screen of the programmer device using the selected time scale as the abscissa in all graphs.

22. A programmer device for displaying an event record of an implantable pacemaker, the event record including a multiplicity of parameters and corresponding parametric data derived from the operation of the implantable pacemaker over a prescribed period of time, the programmer device comprising:

a display screen upon which electronic images may be displayed;

means for receiving pacing event data from the implantable pacemaker;

means for processing the pacing event data received from the implantable pacemaker to produce event records;

a storage element operatively associated with the processing means and adapted for storing the event records;

a means for selecting one of the multiplicity of parameters contained in the event records as a selected parameter to be displayed in a graphical format;

a means for selecting a time scale representing an abscissa of the graphical format in which the selected parameter is to be displayed;

a means for generating and displaying a graphical representation of the parametric data for the selected parameter as an electronic image on the display screen in the graphical format; and a means for displaying a first table of parameters and corresponding parametric data concurrent with the display of the graphical representation of parametric data, with the first table of parametric data corresponding to a selected point of the graphical representation of parametric data;

the graphical representation including an identification mark as part of the display marking the selected point of the graphical representation of parametric data; and a means for selectively scrolling the parametric data included within the graphical representation of parametric data while maintaining the identification mark at a fixed location on the display screen.

23. A method for displaying an event record of an implantable pacemaker using a programmer device, the programmer device having a display screen upon which electronic images may be displayed, the event record including a multiplicity of parameters and corresponding parametric data derived from the operation of the implantable pacemaker, the method comprising the steps of:

downloading pacing event data from the implantable pacemaker to the programmer device;

processing the pacing event data from the implantable pacemaker to produce an event record;

storing the event record in a storage element of the programmer device;

displaying on the display screen a table of parameters and corresponding parametric data associated with the event record;

selecting at least one of the parameters from said table as a selected parameter to be displayed as a graph;

selecting a time scale for an abscissa of the graph to be displayed;

generating and displaying, concurrent with the display of the table of parameters, the graph of the parametric data for the selected parameter using the selected time scale as the abscissa of said graph.

* * * * *